(12) United States Patent
Shuber

(10) Patent No.: US 6,849,403 B1
(45) Date of Patent: Feb. 1, 2005

(54) APPARATUS AND METHOD FOR DRUG SCREENING

(75) Inventor: Anthony P. Shuber, Milford, MA (US)

(73) Assignee: Exact Sciences Corporation, Marlborough, MA (US)

( * ) Notice: Subject to any disclaimer, the term of this patent is extended or adjusted under 35 U.S.C. 154(b) by 0 days.

(21) Appl. No.: 09/724,274

(22) Filed: Nov. 28, 2000

Related U.S. Application Data

(63) Continuation-in-part of application No. 09/455,950, filed on Dec. 7, 1999, now Pat. No. 6,586,177.
(60) Provisional application No. 60/152,847, filed on Sep. 8, 1999, and provisional application No. 60/169,457, filed on Dec. 7, 1999.

(51) Int. Cl.$^7$ ........................... C12Q 1/68; C12P 19/34; C07H 21/04; A61B 5/055

(52) U.S. Cl. ...................... 435/6; 435/91.2; 536/24.33; 424/9.351

(58) Field of Search ................ 435/6, 91.2; 536/24.33; 424/9.351

(56) References Cited

U.S. PATENT DOCUMENTS

| | | | |
|---|---|---|---|
| 3,413,464 A | 11/1968 | Kamentsky | 250/304 |
| 4,101,279 A | 7/1978 | Aslam | 23/259 |
| 4,309,782 A | 1/1982 | Paulin | 4/661 |
| 4,333,734 A | 6/1982 | Fleisher | 23/230 |
| 4,358,535 A | 11/1982 | Falkow et al. | 435/5 |
| 4,445,235 A | 5/1984 | Slover et al. | 4/144.2 |
| 4,535,058 A | 8/1985 | Weinberg et al. | 435/6 |
| 4,578,358 A | 3/1986 | Oksman et al. | 436/66 |
| 4,683,195 A | 7/1987 | Mullis et al. | 435/6 |
| 4,683,202 A | 7/1987 | Mullis | 435/6 |
| 4,705,050 A | 11/1987 | Markham | 128/749 |
| 4,735,905 A | 4/1988 | Parker | 436/174 |
| 4,786,718 A | 11/1988 | Weinberg et al. | 530/387 |
| 4,857,300 A | 8/1989 | Maksem | 424/3 |
| 4,871,838 A | 10/1989 | Bos et al. | 536/27 |
| 4,935,342 A | 6/1990 | Seligson et al. | 435/6 |
| 4,981,783 A | 1/1991 | Augenlicht | 435/6 |
| 4,982,615 A | 1/1991 | Sultan et al. | 73/864.51 |
| 5,087,617 A | 2/1992 | Smith | 514/44 |
| 5,126,239 A | 6/1992 | Livak et al. | 435/6 |
| 5,137,806 A | 8/1992 | LeMaistre et al. | 435/6 |
| 5,149,506 A | 9/1992 | Skiba et al. | 422/102 |
| 5,196,167 A | 3/1993 | Guadagno et al. | 422/56 |
| 5,200,314 A | 4/1993 | Urdea | 435/6 |
| 5,248,671 A | 9/1993 | Smith | 514/44 |
| 5,272,057 A | 12/1993 | Smulson et al. | 435/6 |
| 5,302,509 A | 4/1994 | Cheeseman | 435/6 |
| 5,330,892 A | 7/1994 | Vogelstein et al. | 435/6 |
| 5,331,973 A | 7/1994 | Fiedler et al. | 128/760 |
| 5,348,855 A | 9/1994 | Dattagupta et al. | 435/6 |
| 5,352,775 A | 10/1994 | Albertsen et al. | 536/23.1 |
| 5,362,623 A | 11/1994 | Vogelstein et al. | 435/6 |
| 5,369,004 A | 11/1994 | Polymeropoulos et al. | 435/6 |
| 5,378,602 A | 1/1995 | Polymeropoulos et al. | 435/6 |
| 5,380,645 A | 1/1995 | Vogelstein | 435/6 |
| 5,380,647 A | 1/1995 | Bahar | 435/7.23 |
| 5,382,510 A | 1/1995 | Levine et al. | 435/6 |
| 5,409,586 A | 4/1995 | Kamahori et al. | 204/182.8 |
| 5,416,025 A | 5/1995 | Krepinsky et al. | 436/63 |
| 5,458,761 A | 10/1995 | Kamahori et al. | 204/299 |
| 5,463,782 A | 11/1995 | Carlson et al. | 4/661 |
| 5,466,576 A | 11/1995 | Schulz et al. | 435/6 |
| 5,468,610 A | 11/1995 | Polymeropoulos et al. | 435/6 |
| 5,468,613 A | 11/1995 | Erlich et al. | 435/6 |
| 5,482,834 A | 1/1996 | Gillespie | 435/6 |
| 5,489,508 A | 2/1996 | West et al. | 435/6 |
| 5,492,808 A | 2/1996 | de la Chapelle et al. | 435/6 |
| 5,496,470 A | 3/1996 | Lenhart | 210/222 |
| 5,506,105 A | 4/1996 | Haydock | 435/6 |
| 5,508,164 A | 4/1996 | Kausch et al. | 435/6 |
| 5,512,441 A | 4/1996 | Ronal | 435/6 |
| 5,514,547 A | 5/1996 | Balazs et al. | 435/6 |
| 5,527,676 A | 6/1996 | Vogelstein et al. | 435/6 |
| 5,532,108 A | 7/1996 | Vogelstein | 435/240.2 |
| 5,538,851 A | 7/1996 | Fach et al. | 435/91.2 |
| 5,559,014 A | 9/1996 | Estes et al. | 536/25.42 |
| 5,580,729 A | 12/1996 | Vogelstein | 435/6 |
| 5,589,335 A | 12/1996 | Kearney et al. | 435/6 |
| 5,599,662 A | * 2/1997 | Respess | 435/5 |
| 5,612,473 A | 3/1997 | Wu et al. | 435/240.2 |
| 5,635,352 A | 6/1997 | Urdea et al. | 435/6 |
| 5,641,628 A | 6/1997 | Bianchi | 435/6 |
| 5,645,995 A | 7/1997 | Kieback | 435/6 |
| 5,670,325 A | 9/1997 | Lapidus et al. | 435/6 |

(List continued on next page.)

FOREIGN PATENT DOCUMENTS

| | | |
|---|---|---|
| AU | A-11325/95 | 4/1996 |
| AU | 711754 | 7/1997 |
| AU | 704696 | 8/1997 |

(List continued on next page.)

OTHER PUBLICATIONS

Stratagene Catalog. Gene characterization kits. p. 39, 1988.*
Ambrosini et al. "A novel anti–apoptosis gene, survivin, expressed in cancer and lymphoma" *Nature Medicine,* vol. 3, No. 8, pp. 917–921, Aug. 1997.
Arber et al. "A K–ras Oncogene Increases Resistance to Sulindac–Induced Apoptosis in Rat Enterocytes," *Gastroenterology,* vol. 113, No. 6, pp. 1892–1900, Dec. 1997.
Barry et al. "Identification of Deoxyribonuclease II as an Endonucleas Involved in Apoptosis," *Archives of Biochemistry and Biophysics,* vol. 300, No. 1, pp. 440–450, Jan. 1993.

(List continued on next page.)

*Primary Examiner*—Jeffrey Fredman
*Assistant Examiner*—Brabha Chunduru
(74) *Attorney, Agent, or Firm*—Testa, Hurwitz & Thibeault, LLP

(57) ABSTRACT

The present invention provides kits and methods for screening drugs and drug candidates for activity by determining the presence or absence of high integrity nucleic acid in a sample.

26 Claims, 3 Drawing Sheets

U.S. PATENT DOCUMENTS

| | | | |
|---|---|---|---|
| 5,688,643 A | 11/1997 | Oka et al. ................. | 435/6 |
| 5,709,998 A | 1/1998 | Kinzler et al. ............ | 435/6 |
| 5,710,028 A | 1/1998 | Eyal et al. ................ | 435/91.1 |
| 5,741,650 A | 4/1998 | Lapidus et al. ........... | 435/6 |
| 5,759,777 A | 6/1998 | Kearney et al. ........... | 435/6 |
| 5,830,665 A | 11/1998 | Shuber et al. ............ | 435/6 |
| 5,846,710 A | 12/1998 | Bajaj ....................... | 435/6 |
| 5,856,104 A | 1/1999 | Chee et al. ............... | 435/6 |
| 5,882,865 A | 3/1999 | Vogelstein et al. ....... | 433/6 |
| 5,888,778 A | 3/1999 | Shuber ..................... | 435/6 |
| 5,910,407 A | 6/1999 | Vogelstein et al. ....... | 435/6 |
| 5,916,744 A | 6/1999 | Taylor ...................... | 435/6 |
| 5,928,870 A | 7/1999 | Lapidus et al. ........... | 435/6 |
| 5,942,396 A | 8/1999 | Shiff et al. ................ | 435/6 |
| 5,952,178 A | 9/1999 | Lapidus et al. ........... | 435/6 |
| 5,976,800 A | 11/1999 | Lau et al. ................. | 435/6 |
| 6,020,137 A | 2/2000 | Lapidus et al. ........... | 435/6 |
| 6,037,465 A | 3/2000 | Hillebrand et al. ....... | 536/25.42 |
| 6,084,091 A | 7/2000 | Müller et al. | |
| 6,100,029 A | 8/2000 | Lapidus et al. ........... | 435/6 |
| 6,143,529 A * | 11/2000 | Lapidus et al. ........... | 435/91.2 |
| 6,146,828 A | 11/2000 | Lapidus et al. ........... | 435/6 |
| 6,150,100 A | 11/2000 | Rüschoff et al. | |
| 6,156,504 A * | 12/2000 | Gocke et al. ............. | 435/6 |
| 6,177,251 B1 | 1/2001 | Vogelstein et al. ....... | 435/6 |
| 6,203,993 B1 | 3/2001 | Shuber et al. ............ | 435/6 |
| 6,214,187 B1 | 4/2001 | Hammond et al. ....... | 204/450 |
| 6,214,558 B1 | 4/2001 | Shuber et al. ............ | 435/6 |
| 6,238,927 B1 | 5/2001 | Abrams et al. ........... | 436/94 |
| 6,251,660 B1 | 6/2001 | Muir et al. ............... | 435/287.2 |
| 6,268,136 B1 | 7/2001 | Shuber et al. ............ | 435/6 |
| 6,280,947 B1 | 8/2001 | Shuber et al. ............ | 435/6 |
| 6,300,077 B1 | 10/2001 | Shuber et al. ............ | 435/6 |
| 6,303,304 B1 | 10/2001 | Shuber et al. ............ | 435/6 |
| 6,351,857 B2 | 3/2002 | Sloan, III et al. ......... | 4/315 |
| 6,406,857 B1 | 6/2002 | Shuber et al. ............ | 435/6 |
| 6,415,455 B1 | 7/2002 | Sloan, III et al. ......... | 4/315 |
| 6,428,964 B1 | 8/2002 | Shuber ..................... | 435/6 |
| 6,448,002 B1 | 9/2002 | Hillebrand et al. | |
| 6,475,738 B2 | 11/2002 | Shuber et al. ............ | 435/6 |
| 6,482,595 B2 | 11/2002 | Shuber et al. ............ | 435/6 |
| 6,503,718 B2 | 1/2003 | Shuber et al. | |
| 2001/0018180 A1 | 8/2001 | Shuber et al. ............ | 435/6 |
| 2002/0025525 A1 | 2/2002 | Shuber ..................... | 435/6 |
| 2002/0110810 A1 | 8/2002 | Shuber ..................... | 435/6 |
| 2002/0119469 A1 | 8/2002 | Shuber et al. ............ | 435/6 |
| 2002/0119472 A1 | 8/2002 | Lapidus et al. ........... | 435/6 |
| 2002/0132251 A1 | 9/2002 | Shuber ..................... | 435/6 |
| 2002/0164631 A1 | 11/2002 | Shuber et al. ............ | 435/6 |

FOREIGN PATENT DOCUMENTS

| | | | |
|---|---|---|---|
| AU | 745862 | 9/1998 | |
| AU | 744746 | 1/1999 | |
| AU | 720489 | 9/1999 | |
| AU | 199942333 A1 | 9/1999 | |
| CA | 2228769 | 2/1997 | |
| CA | 2211702 | 5/1999 | |
| DE | 195 30 132 A | 2/1997 | |
| DE | 195 30 132 C2 | 2/1997 | |
| DE | 197 36 691 A | 2/1999 | |
| EP | 0 270 017 A3 | 6/1988 | |
| EP | 0 270 017 A2 | 6/1988 | |
| EP | 0 270 017 | 6/1988 | ................. 1/8 |
| EP | 0 284 362 A3 | 9/1988 | |
| EP | 0 284 362 A2 | 9/1988 | |
| EP | 0 337 498 A2 | 10/1989 | |
| EP | 0 390 323 A3 | 10/1990 | |
| EP | 0 390 323 A2 | 10/1990 | |
| EP | 0 391 565 B1 | 10/1990 | |
| EP | 0 391 565 A2 | 10/1990 | |
| EP | 0 407 789 B1 | 1/1991 | |
| EP | 0 407 789 A1 | 1/1991 | |
| EP | 0 608 004 A2 | 7/1994 | |
| EP | 0 259 031 B1 | 11/1994 | |
| EP | 0 648 845 A | 4/1995 | |
| EP | 0 664 339 A1 | 7/1995 | |
| EP | 0 664 339 | 7/1995 | |
| GB | 2327497 A | 1/1999 | |
| JP | 3325270 | 9/2002 | |
| WO | WO 90/09455 | 8/1990 | |
| WO | WO 92/13103 | 8/1992 | |
| WO | WO 92/16657 | 10/1992 | |
| WO | WO 93/18186 | 9/1993 | |
| WO | WO 93/20233 | 10/1993 | |
| WO | WO 93/20235 | 10/1993 | |
| WO | WO 94/00603 | 1/1994 | |
| WO | WO 94/01447 | 1/1994 | |
| WO | WO 94/09161 | 4/1994 | |
| WO | WO 94/10575 | 5/1994 | |
| WO | WO 94/11383 | 5/1994 | |
| WO | WO 95/00669 | 1/1995 | |
| WO | WO 95/07361 | 3/1995 | |
| WO | WO 95/09928 | 4/1995 | |
| WO | WO 95/09929 | 4/1995 | |
| WO | WO 95/12606 | 5/1995 | |
| WO | WO 95/13397 | 5/1995 | |
| WO | WO 95/15400 | 6/1995 | |
| WO | WP 95/16792 | 6/1995 | |
| WO | WO 95/18818 | 7/1995 | |
| WO | WO 95/19448 | 7/1995 | |
| WO | WO 95/25813 | 9/1995 | |
| WO | WO 95/31728 | 11/1995 | |
| WO | WO 96/01907 | 1/1996 | |
| WO | WO 96/06951 | 3/1996 | |
| WO | WO 96/08514 | 3/1996 | |
| WO | WO 96/12821 | 5/1996 | |
| WO | WO 96/13611 | 5/1996 | |
| WO | WO 96/23895 | 8/1996 | |
| WO | WO 96/29430 | 9/1996 | |
| WO | WO 96/30545 | 10/1996 | |
| WO | WO 97/07239 | 2/1997 | ................. 1/68 |
| WO | WO 97/09449 | 3/1997 | |
| WO | WO 97/09600 A3 | 3/1997 | |
| WO | WO 97/09600 A2 | 3/1997 | |
| WO | WO 97/19191 | 5/1997 | |
| WO | WO 97/23651 | 7/1997 | |
| WO | WO97/25442 | 7/1997 | |
| WO | WO 97/28450 | 8/1997 | |
| WO | WO 98/08971 | 3/1998 | ................. 1/68 |
| WO | WO 98/38338 | 9/1998 | |
| WO | WO 98/39478 | 9/1998 | |
| WO | WO 98/58081 | 12/1998 | |
| WO | WO 98/58084 | 12/1998 | |
| WO | WO 99/07894 | 2/1999 | |
| WO | WO 99/07895 | 2/1999 | |
| WO | WO 99/10528 | 3/1999 | |
| WO | WO 99/20798 | 4/1999 | |
| WO | WO99/26724 | 6/1999 | |
| WO | WO 99/28507 | 6/1999 | |
| WO | WO99/45374 | 9/1999 | |
| WO | WO 99/53316 | 10/1999 | |
| WO | WO 99/55912 | 11/1999 | |
| WO | WO 99/66077 | 12/1999 | |
| WO | WO99/66078 | 12/1999 | |
| WO | WO99/66079 | 12/1999 | |
| WO | WO 00/09751 | 2/2000 | |
| WO | WO 00/11215 | 3/2000 | |
| WO | WO 00/31298 | 6/2000 | |
| WO | WO 00/31303 | 6/2000 | |
| WO | WO 00/31305 | 6/2000 | |

| WO | WO 00/32820 | 6/2000 | |
| --- | --- | --- | --- |
| WO | WO 01/42503 A3 | 7/2000 | ............... 9/38 |
| WO | WO 00/50640 | 8/2000 | |
| WO | WO00/50870 | 8/2000 | |
| WO | WO 00/58514 | 10/2000 | |
| WO | WO00/60118 | 10/2000 | |
| WO | WO 00/61808 | 10/2000 | |
| WO | WO 00/66005 | 11/2000 | |
| WO | WO 00/70096 A3 | 11/2000 | |
| WO | WO 00/70096 | 11/2000 | |
| WO | WO 01/11083 A3 | 2/2001 | |
| WO | WO 01/11083 | 2/2001 | |
| WO | WO 01/18252 | 3/2001 | |
| WO | WO 01/42502 | 6/2001 | |
| WO | WO 01/42502 A2 | 6/2001 | ............... 1/68 |
| WO | WO 01/42503 | 6/2001 | |
| WO | WO 01/42781 | 6/2001 | |
| WO | WO 01/64950 A2 | 9/2001 | ............... 1/68 |
| WO | WO02/055740 A2 | 7/2002 | |
| WO | WO02/059379 A2 | 8/2002 | |
| WO | WO02/074995 A1 | 9/2002 | |
| WO | WO02/092858 A2 | 11/2002 | |

OTHER PUBLICATIONS

Bernstein et al. "A Bile Acid–induced Apoptosis Assay for Colon–Cancer Risk and Associated Quality Control Studies," *Cancer Research,* vol. 59, pp. 2353–2357, May 15, 1999.

Croitoru et al. "Reduce, Reuse, and Recycle: Shedding Light on Shedding Cells," *Gastroenterology,* vol. 105, pp. 1243–1246, Oct. 1993.

Depraetere, "Eat me– Signals of apoptotic bodies," *Nature Cell Biology,* vol. 2, p. E104, Jun. 2000.

Finkel "Does Cancer Therapy Trigger Cell Suicide?," *Science,* vol. 286, pp. 2256–2258, Dec. 17, 1999.

Garewal et al. "Reduced Bile Acid–induced Apoptosis in "Normal" Colorectal Mucosa: A Potential Biological Marker for Cancer Risk" *Cancer Research,* vol. 56, pp. 1480–1483, Apr. 1, 1996.

Halim, "Apoptosis: Orderly Dismantling" *The Scientist,* p. 19, Feb. 7, 2000.

Hall et al. "Regulation of cell number in the mammalian gastrointestinal tract: the importance of apoptosis," *Journal of Cell Science,* vol. 107, pp. 3569–3577, 1994.

Hetts, "To Die or Not to Die, An Overview of Apoptosis and Its Role in Disease," *JAMA,* vol. 279, No. 4, pp. 300–307, Jan. 28, 1998.

Hitchcock, "Actin–Deoxyribonuclease I Interaction," *The Journal of Biochemical Chemistry,* vol. 255, No. 12, pp. 5668–5673, 1980.

Iwanaga et al. "A Novel Mechanism for Disposing of Effete Epithelial Cells in the Small Intestine of Guinea Pigs," *Gastroenterology,* vol. 105, No. 4, pp. 1089–1097, 1993.

Kataoka et al. "Association of high molecular weight DNA fragmentation with apoptotic or non–apoptotic cell death induced by calcium ionophore" *FEBS Letters,* vol. 364, pp. 264–267, 1995.

Kawasaki et al. "Inhibition of Apoptosis by Survivin Predicts Shorter Survival Rates in Colorectal Cancer," *Cancer Research,* vol. 58, pp. 5071–5074, Nov. 15, 1998.

Kishi et al. "Human Serum Deoxyribonuclease I (DNase I) Polymorphism: Pattern Similarities among Isozymes from Serum, Urine, Kidney, Liver, and Pancreas," *Am. J. Hum. Genet.,* vol. 47, pp. 121–126, 1990.

Komano et al. "Homeostatic regulation of intestinal epithelia by intrepithelial γδ T cells" *Proc. Natl. Acad. Sci, USA 92,* vol. 92, pp. 6147–6151, Jun. 1995.

Lipkin, "Biomarkers of Increased Susceptibility to Gastrointestinal Cancer: New Application to Studies of Cancer Prevention in Human Subjects," *Cancer Research,* vol. 48, pp. 235–245, Jan. 15, 1998.

Mannherz et al. "A Specific 1:1 G–Actin: DNAase I Complex Formed by the Action of DNAase I on F–Actin," *FEBS Letters,* vol. 60, No. 1, pp. 34–38, Dec. 1975.

Manherz et al. "The Interaction of Bovine Pancreatic Deoxyribonuclease I and Skeletal Muscle Actin" *Eur. J. Biochem,* vol. 104, pp. 367–379, 1980.

Park et al. "Detergent and Enzyme Treatment of Apoptotic Cells for Observation of DNA Fragmentation" *BioTechniques,* vol. 24, No. 4, pp. 558–559, 1998.

Payne et al. "Role of Apoptosis in Biology and Pathology: Resistance to Apoptosis in Colon Carcinogenesis" *Ultrastructural Pathology,* vol. 19, pp. 221–248, 1995.

Peitsch et al. "Characterization of the endogenous deoxyribonuclease involved in nuclear DNA degradation during apoptosis (programmed cell death)," *The EMBO Journal,* vol. 12, No. 1, pp. 371–377, 1993.

Peitsch et al. "Functional characterisation of serum DNase I in MRI," *Biochemical and Biophysical Research Communications,* vol. 186, No. 2, pp. 739–745, Jul. 31, 1992.

Peitsch et al. "The apoptosis endonucleases: cleaning up after cell death?, "*Trends in Cell Biology,* vol., 4, pp. 37–41, Feb. 4, 1994.

Polzar et al. "Distribution of deoxyribonuclease I in rat tissues and its correlation to cellular turnover and apoptosis (programmed cell death)," *European Journal of Cell Biology,* vol. 64, pp. 200–210, 1994.

Polzar et al. "Overexpression of deoxyribonucelase I (DNase I) transfected into COS–cells: its distribution during apoptotic cell death," *European Journal of Cell Biology,* vol. 62, pp. 397–405, 1993.

Saitoh et al. "Analysis of Bcl–2, Bax and Survivin genes in uterine cancer" *International Journal of Oncology,* vol. 15, pp. 137–141, 1999.

Sen "Programmed Cell Death: Concept, Mechanism and Control" *Biol. Rev.,* vol. 67, pp. 287–319, 1992.

Sträter et al. "Rapid Onset of Apoptosis In Vitro Follows Disruption of B1 Integrin/Matrix interactions in Human Colonic Crypt Cell" *Gastroenterology,* vol. 110, No. 6, pp. 1776–1784, Jun. 1996.

Tsujitani et al. "Apoptotic Cell Death and Its Relationship to Carcinogenesis in Colorectal Carcinoma," *Cancer Supplement,* vol. 77, No. 8, pp. 1711–1716, Apr. 15, 1996.

Wagner et al. "Regulation of Gastric Epithelial Cell Growth by Helicobacter pylori: Evidence for a Major Role of Apoptosis," *Gastroenterology,* vol. 113, No. 6, pp. 1836–1847, Dec. 1997.

Zhang et al. "Quantitative determination of apoptotic death in cultured human pancreatic cancer cells by propidium iodide and digitonin," *Cancer Letters,* vol. 142, pp. 129–137, 1999.

Skoletsky, J.E. et al.: "High Frequency of Detecting Amplifiable DNA in Stools of Apparently Normal Individuals" *Gastroenterology,* Maynard, MA, USA,, vol. 114, No. 4, p. A681 (Apr. 1998).

Eads et al. (1990), "CpG Island Hypermethylation in Human Colorectal Tumors is Not Associated with DNA Methyltransferase Overexpression" *Cancer Research* 59:2302–2306.

Giacona et al. (1998), "Cell–Free DNA in Human Blood Plasma: Length Measurements in Patients with Pancreatic Cancer and Healthy Controls" *Pancreas* 17:89–97.

International Search Report for International Patent Application Serial No. PCT/US00/32387, dated Jul. 17, 2001, 5 pages.

Allen et al. (1997), "Morphological and biochemical characterization and analysis of apoptosis." *J. Pharm & Toxicol. Methods,* vol. 37, No. 4, pp. 215–228.

Anker et al., (1999), "Detection of Circulating Tumour DNA in the Blood (plasma/serum) of Cancer Patients." *Cancer and Metastasis Reviews,* vol. 18, pp. 65–73.

Cawkwell et al. (1994), "Frequency fo allele loss of DCC, p53, RB1, WT1, NF1, NM23 and APC/MCC in colorectal cancer assayed by fluorescent multiplex polymerase chain reaction." *Brit. J. Can.,* vol. 70, No. 5, pp. 813–818.

Dennin, (1979), "DNA of Free and Complexed Origin in Human Plasma: Concentration and Length Distribution." *Klin. Wochenschr,* vol. 57, pp. 451–456.

Ditkoff et al. (1996), "Detection of circulating thyroid cells in peripheral blood." *Surgery* vol. 120, No. 6, pp. 959–965.

Emlen et al., (1984), "Effect of DNA Size and Strandedness on the in vivo Clearance and Organ Localization of DNA," *Clin. Exp. Immunol,* vol. 56, pp. 185–192.

Fournie et al., (1995), "Plasma DNA as a Marker of Cancerous Cell Death. Investigations in Patients Suffering from Lung Cancer and in Nude Mice Bearing Human Tumours," *Cancer Letters,* vol. 91, pp. 221–227.

Hibi et al., (Apr. 1998), "Molecular Detection of Genetic Alterations in the Serum of Colorectal Cancer Patients," *Cancer Research,* vol. 58, pp. 1405–1407.

Ito et al., (1999), "Profile of Circulating Levels of Interleukin–1 Receptor Antagonist and Interleukin–6 in Colorectal Cancer Patients." *Scand. J. Gastroentero.,* vol. 11, pp. 1139–1143.

Leon et al., (Mar. 1977), "Free DNA in the Serum of Cancer Patients and the Effect of Therapy," *Cancer Research,* vol. 37, pp. 646–650.

Maebo, (1990), "Plasma DNA Level as a Tumor Marker in Primary Lung Cancer," Japanese; English abstract attached.

Mulcahy et al. (1998), "A prospective study of K–ras mutations in the plasma of pancreatic cancer patients." *Clin. Cancer Res.,* vol. 4, pp. 271–275.

Raptis et al., (Dec. 1980), "Quantitation and Characterization of Plasma DNA in Normals and Patients with Systemic Lupus Erythematosus." *J. Clin. Invest.,* vol. 66, pp. 1391–1399.

Sales et al., (Jul. 31, 1999), "Blood Dissemination of Colonic Epithelial Cells During No–touch Surgery for Rectosigmoid Cancer." *The Lancet,* vol. 354, p. 342.

Schmitt et al. (1998), "Bax–alpha promotes apoptosis induced by cancer chemotherapy and accelerates the activation of caspase 3–like cysteine proteases in p53 double mutant B lymphoma Namalwa cells." *Cell Death & Diff.,* vol. 5, No. 6, pp. 506–516.

Shapiro et al., (Jun. 1, 1983), "Determination of Circulating DNA Levels in Patients with Benign or Malignant Gastrointestinal Disease." *Cancer,* vol. 51, No. 11, pp. 2116–2120.

Sidransky, D. (1997) "Nucleic acid–based methods for the detection of cancer." *Science,* vol. 278, No. 5340, pp. 1054–1057.

Stroun et al., (1987), "Isolation and Characterization of DNA from the Plasma of Cancer Patients." *Eur. J. Cancer Clin. Oncol.,* vol. 23, No. 6, pp. 707–712.

Vet et al., (1998) "Comparative analysis of p53 mutations in bladder washings and histologic specimens." *Am. J. Clin. Path.,* vol. 110, No. 5, pp. 647–652.

Zhou et al. (1997) "Allelic Profiles of Mononucleotide Repeat Microsatellites in Control Individuals and in Colorectal Tumors With and Without Replication Errors" *Oncogene* 15: 1713–1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21: 101–107.

Vasen et al. (1998) "A Cost–Effectiveness Analysis of Colorectal Screening of Hereditary Nonpolyposis Colorectal Carcinoma Gene Carriers" *American Cancer Society* 82: 1632–1637.

Vasen et al. (1999) "New Clinical Criteria for Hereditary Nonpolyposis Colorectal Cancer (HNPCC, Lynch Syndrome) Proposed by the International Collaborative Group on HNPCC" *Gastroenterology* 116: 1453–1456.

Vera–Garcia, et al., (May 16–20, 1993) "Development and Evaluation of an Instrument Designed to Reproducibly Release Nucleic Acids from Microorganisms" *American Society for Microbiology: Polymerase Chain Reaction,* $93^{rd}$ General Meeting, Session 214, Abstract C–217, p. 484.

Villa et al., (May 1996) "Identification of Subjects at Risk for Coloretal Carcinoma Through a Test Based on K–ras Determination in the Stool," *Gastroenterology,* vol. 110, No. 5, pp. 1346–1353.

Vogelstein, B. and Kinzler, K.W., (Aug., 1999) "Digital PCR," *Proc. Natl. Acad. Sci. USA,* vol. 96, pp. 9236–9241.

Vogelstein et al., (1979) "Preparative and Analytical Purification of DNA from Agarose," *Proc. Natl. Acad. Sci. USA,* vol. 76, No. 2, pp. 615–619.

Wallace et al., (1979) "Hybridization of Synthetic Oligodeoxyribonucleotides to $\Phi\chi$ 174 DNA: the Effect of Single Base Pair Mismatch," *Nucleic Acids Research,* vol. 6, No, 11, pp. 3543–3557.

Walsh et al., (1991) "Chelex® 100 as a Medium for Simple Extraction of DNA for PCR–Based Typing from Forensic Material," *BioTechniques,* vol. 10, No. 4, pp. 506–513.

Walsh et al., (Feb. 6, 1992) "Preferential PCR Amplification of Alleles: Mechanisms and Solutions," *PCR Methods and Applications,* pp. 241–250.

Walton et al., (1997) "A PCR–Based Method for Detecting Rare Genotypes in Large Samples of Individuals," *Mol. Ecology,* vol. 6, No. 2, pp. 195–197.

Wang et al., (May 15, 1998) "Large–Scale Identification, Mapping, and Genotyping of Single–Nucleotide Olymorphisms in the Human Genome," *Science,* vol. 280, pp. 1077–1082.

Watson et al., "Isolation of Differentiality Expressed Sequence Tags from Human Breast Cancer," *Advances in Brief XP 000576043,* pp. 4598–4602.

Wijnen et al. (1999) "Familial Endometrial Cancer in Female Carriers of MSH6 Germline Mutations" *Nature Genetics* 23: 142–144.

Young G.P., and B.H. Demediu, (1992) "The Genetics, Epidemiology, and Early Detection of Gastrointestinal Cancers" *Current Opinion in Oncology,* vol. 4, pp. 728–735.

Samowitz et al. (1997) "Microstaellite Instability in Colorectal Adenomas" *Gastroenterology* 112: 1515–1519.

Samowitz et al. (1999) "BAT–26 and BAT–40 Instability in Colorectal Adenomas and Carcinomas and Germline Polymorphisms" *American Journal of Pathology* 154: 1637–1641.

Samiotaki et al. (1994), "Dual–Color Detection of DNA Sequence Variants by Ligase–Mediated Analysis," *Genomics* 20:238–42.

Sanger et al., (Dec. 1977) "DNA Sequencing with Chain–Terminating Inhibitors" *Proc. Natl. Acad. Sci. USA,* vol. 74, No. 12, pp. 5463–5467.

Santagati et al., "Quantiation of low abundance mRNAs in glial cells using different polymerase chain reaction (PCR)–based methods" *Brain Research Protocols,* vol. 1, 1997, pp. 271–223 XP000892447.

Segel I., (1976), "Double Label Analysis," *Biochemical Calculations,* 2d ed., pp. 373–376.

Shaw et al., (1998) "Allele Frequency Distribution in Pooled DNA Samples, Applications to Mapping Complex Disease Genes," *Genome Research,* vol. 8, pp. 111–123m.

Sidransky, et al., (Apr. 3, 1992) "Identification of ras Oncogene Mutations in the Stool of Patients with Curable Colorectal Tumors," *Science,* vol. 256, pp. 102–105.

Smith–Ravin et al., (1995) "Detection of c–Ki–ras Mutations in Faecal Samples from Sporadic Colorectal Cancer Patients," *Gut,* vol. 36, pp. 81–86.

Supplemental Information, ProCipitate and Cleanascite, LigoChem, Inc., Fairfield, NJ (Date unknown).

Syngal et al. (1998) "Benefits of Colonoscopic Surveillance and Prophylactic Colectomy in Patients With Hereditary Nonpolyposis Colorectal Cancer Mutations" *Annals of Internal Medicine* 129: 787–796.

Syngal et al. (1999) "Interpretation of Genetic Test Results for Hereditary Nonpolyposis Colorectal Cancer" *JAMA* 282:247.

Takeda et al., (1993) "Detection of K–ras Mutation in Sputum by Mutant–Allele–Specific Amplification (MASA)," *Human Mutation,* vol. 2, pp. 112–117.

Thibodeau et al., (May 7, 1993) "Microsatellite Instability in Cancer of the Proximal Colon," *Science,* vol. 260, pp. 816–819.

Tompkins et al., (1986) "Approaches to the Detection of Enteric Pathogens, Including Campylobacter using Nucleic Acid Hybridization," *Diagn. Microbiol, Infect. Dis.,* vol. 4, pp. 715–785.

Vasen et al. (1993) "Surveillance in Hereditary Nonpolyposis Colorectal Cancer: An International Cooperative Study of 165 Families" *Diseases of the Colon & Rectum*) 36:1–4.

Piao et al., (Sep 1997) "Relationship between Loss of Heterozygosity of Tumor Suppressor Genes and Histologic Differentiation in Hepatocellular Carcinoma," *Cancer,* vol. 80, No. 5, pp. 865–872.

Ponz de Leon et al. (1998) "Frequency and Type of Colorectal Tumors in Asymptomatic High–Risk Individuals in Families with Hereditary Nonpolyposis Colorectal Cancer" *Cancer Epidemiology, Biomarkers & Prevention* 7: 639–641.

Ponz de Leon et al. (1999) "Hereditary Colorectal Cancer in the General Population: From Cancer Registration to Molecular Diagnosis" *Gut* 45: 32–38.

Pyatt et al. (1999) "Polymorphic Variation at the BAT–25 and BAT–26 Loci in Individuals of African Origin" *American Journal of Pathology* 155: 349–353.

Raff, M., (Nov. 12, 1998) "Cell Suicide for Beginners," *Nature,* vol. 396, pp. 119–122.

Rashid et al. (1999) "Genetic Epidemiology of Mutated K–ras Proto–Oncogene, Altered Suppressor Genes, and Microsatellite Instability in Colorectal Adenomas" *Gut* 44:826–833.

Ravelingien et al., (1995) "Contribution of Molecular Oncology in the Detection of Colorectal Carcinomas," *Acta Gastro–Enterologica Belgica,* vol. 58, pp. 270–273.

Rhyu M. S., (Mar. 6, 1996) "Molecular Mechanisms Underlying Hereditary Nonpolyposis Colorectal Carcinoma," *Journal of the National Cancer Institute,* vol. 88, No. 5, pp. 240–251.

Riegler et al. (1999) "Prevalence of HNPCC in a Series of Consecutive Patients on the First Endoscopic Diagnosis of Colorectal Cancer: A Multicenter Study" *Endoscopy* 31: 337–341.

Ridanpaa et al., (1995) "Detection of Loss of Heterozygosity in the p53 Tumor Suppressor Gene Using a PR–based Assay," *Path. Res. Pract.,* vol. 191, pp. 399–402.

Rinaldy et al. (1988), "Gene Cloning Using cDNA Libraries in a Differential Competition Hybridization Strategy: Application to Cloning XP–A Related Genes," *DNA* 7(8):563–70.

Rodriguez–Bigas et al. (1997) "A National Cancer Institute Worship on Hereditary Nonpolyposis Colorectal Cancer Syndrome: Meeting Highlights and Bethesda Guidelines" *Journal of the National Cancer Institute* 89: 1758–1762.

Ruzicka et al., (1992) "Apolipoprotein Allele Specific PCR: Large–Scale Screening of Pooled Blood Samples," *J. of Lipid Research,* vol. 33, pp. 1563–1567.

Salahshor et al. (1999) "Microsatellite Instability in Sporadic Colorectal Cancer is Not an Independent Prognostic Factor" *British Journal of Cancer* 81: 190–193.

Samowitz et al. (1995) "Microsatellite Instability in Human Colonic Cancer Is Not a Useful Clinical Indicator of Familial Colorectal Cancer" Gastroenterology 109: 1765–1771.

Lamberti et al., (1999) "Microsatellite Instability—a Useful Diagnostic Tool to Select Patients at High Risk for Hereditary Non–Polyposis Colorectal Cancer: A Study in Different Groups of Patients With Colorectal Cancer" *Gut* 44: 839–843.

Lefrere et al., (Oct. 1998) "Screening Blood Donations for Viral Genomes: Multicenter Study of Real–Time Simulation Using Pooled Samples on the Model of HCV RNA Detection" *Transfusion,* vol. 38, pp. 915–923.

Lengauer et al., (Dec. 17, 1998) "Genetic Instabilities in Human Cancers," *Nature,* vol. 396, pp. 643–649.

Leong et al., (1993) "Detection of MYCN Gene Amplificaiton and Deletions of Chromosome 1p in Neuroblastoma by In Situ Hybridization Using Routing Histologic Sections," *Laboratory Investigations,* vol. 69, No. 1, pp. 43–50.

Li et al., (Aug. 1996) "Rapid Detection of Mycobacterium Avium in Stool Samples from AIDS Patients by Immunomagnetic PCR," *J. Clin. Microbiol.,* vol. 34, No. 8, pp. 1903–1907.

Lin et al. (1998) "Colorectal and Extracolonic Cancer Variations in MLH1/MSH2 Hereditary Nonpolyposis Colorectal Cancer Kindreds and the General Population" *Diseases of the Colon & Rectum* 41: 428–433.

Litia et al., (1992) "Simultaneous Detection of Two Cystic Fibrosis Alleles Using Dual–Label Time–Resolved Fluorometry," *Molecular and Cellular Probes,* vol. 6, pp. 505–512.

Lleonart et al. (1998) "Microsatellite Instability and p53 Mutations in Sporadic Right and Left Colon Carcinoma" *American Cancer Society* 83: 889–895.

Loktionov A. and I. K. O'Neill, (1995) "Early Detecion of Cancer–Associated Gene Alterations in DNA Isolated from Rat Feces During Intestinal Tumor Induction with 1,2–Dimethylhydrazine," *International Journal of Oncology,* vol. 6, pp. 437–445.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research,* vol. 4, pp. 337–341.

Mao, L. et al., (Feb. 2, 1996) "Molecular Detection of Primary Bladder Cancer by Microsatellite Analysis," *Science,* vol. 271, pp. 659–662.

Metspalu A., "Arrayed Primer Extension (APEX) for Mutation Detection Using Gene–Specific DNA Chips" *European Journal of Human Genetics,* vol. 6, No. Sup 1, 1998, p. PL36 XP000892253 Abstract.

Morandi et al., (Jun. 1998) "Detection of HIV Type 1 RNA in Pools of Sera Negative for Antiobiotics to HIV–1 and HIV–2," *J. of Clinical Microbiology,* vol. 36, No. 6, pp. 1534–1538.

Aaltonen et al. (1994) "Replication Errors in Benign and Malignant Tumors from Hereditary Nonpolyposis Colorectal Cancer Patients" *Cancer Research* 54: 1645–1648.

Aaltonen et al. (1998) "Incidence of Hereditary Nonpolyposis Colorectal Cancer and the Feasibility of Molecular Screening for the Disease" *The New England Journal of Medicine* 338: 1481–1487.

Ausubel et al., (1995), *Short Protocols in Molecular Biology,* 3d ed., pp. 2–3–2–12, 2–23–2–24, 3–30–3–33.

Azhikina et al. (1996), "Factors Affecting the Priming Efficiency of Short Contiguous Oligonucleotide Strings in the Primer Walking Strategy of DNA Sequencing," *DNA Sequence* 6:211–16.

Bertario et al. (1999) "Risk of Colorectal Cancer Following Colonoscopic Polypectomy" *Tumori* 85: 157–162.

Beskin et al., (1995), "On the Mechanism of the Modular Primer Effect," *Nucleic Acids Research,* vol. 23, No. 15, 2881–2885.

Blu, H.E., (1995) "Colorectal Cancer: Future Population Screening for Early Colorectal Cancer" *European Journal of Cancer,* vol. 31A, pp. 1369–1372.

Boom et al., (Mar. 1990) "Rapid and Simple Method for Purification of Nucleic Acids" *J. Clin. Microbiol.,* vol. 28, No. 3, pp. 495–503.

Bos et al., (May 28, 1987) "Prevalence of ras Gene Mutations in Human Colorectal Cancers," *Nature,* vol. 327, pp. 293–297.

Caldas et al., (Jul. 1, 1994) "Detection of K–ras Mutations in the Stool of Patients with Pancreatic Adenocarcinoma and Pancreatic Ductal Hyperplasia", *Cancer Research,* vol. 54, pp. 3568–3573.

Capozzi et al. (1999) "Evaluation of the Replication Error Phenotype in Relation to Molecular and Clinicopathological Features in Hereditary and Early Onset Colorectal Cancer" *European Journal of Cancer* 35: 289–295.

Cave et al., (1994) "Reliability of PCR Directly from Stool Samples: Usefulness of an Internal Standard," *BioTechniques,* vol. 16, No. 5, pp. 809–810.

Chapelle (1999) "Testing Tumors for Microsatellite Instability" *European Journal of Human Genetics* 7: 407–408.

Charlesworth et al., (Sep. 15, 1994) "The Evolutionary Dynamics of Repetitive DNA in Eukaryotes," *Nature,* vol. 371, pp. 215–220.

Chen et al., (Jul. 15, 1996) "Detection of Single–Base Mutations by a Competitive Mobility Shift Assay," *Analytical Biochemistry, US, Academic, Press,* vol. 239, No. 1, pp. 61–69.

Chen et al. (1997) "Microsatellite Instability in Sporadic–Colon–Cancer Patients With and Without Liver Metastases" *International Journal of Cancer* 74: 470–474.

Coombs et al., (May 21, 1996) "A Rapid, Simple, and User–Friendly Method for DNA Extraction from Clinical Stool Samples," *ASM 1996 General Meeting,* New Orleans, LA.

Cohen, S., (Mar. 22, 1996) "Human Nucleic Acid Extraction from Stool and Hybridization Protocols" (3 pages).

Coll et al., (Oct. 1989) "Evaluation of a Rapid Method of Extracting DNA from Stool Samples for Use in Hybridization Assays," *Journal of Clinical Microbiology,* vol. 27, No. 10, pp. 2245–2248.

Coughlin et al. (1999) "Public Health Perspectives on Testing for Colorectal Cancer Susceptibility Genes" *American Journal of Preventive Medicine* 16: 99–104.

Cunningham C. and M.G. Dunlop, (1996) "Molecular Genetic Basis of Colorectal Cancer Susceptibility," *British Journal of Surgery,* vol. 83, pp. 321–329.

Deng et al., (Dec. 20, 1996) "Loss of Heterozygosity in Normal Tissue Adjacent to Breast Carcinomas," *Science,* vol. 274, pp. 2057–2059.

Deuter et al., (1995) "A Method for Preparation of Fecal DNA Suitable for PCR," *Nucleic Acids Research,* vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now be Used for Early Diagnosis of Malignancy?" *Clin. Chem,.* vol. 41, No. 10, pp. 1410–1413.

Echeverria et al., (Sep. 1985) "DNA Hybridization in the Diagnosis of Bacterial Diarrhea," *Clinics in Laboratory Medicine,* vol. 5, No. 3, Sep. 1985, pp. 447–462.

Eguchi et al., (Apr. 15, 1996) "Mutations of the p53 Gene in the Stool of Patients with Resectable Colorectal Cancer," *Cancer Supplement,* vol. 77, No. 8, pp. 1707–1710.

Enari et al., (Jan. 1, 1998) "A Caspase–Activated DNase that Degrades DNA During Apoptosis, and its Inhibitor ICAD," *Nature,* vol. 391, pp. 43–50.

Fearon, E.R., (1995) "16 Molecular Abnormalities in Colon and Rectal Cancer," *The Molecular Basis of Cancer,* pp. 340–357.

Grossman et al. (1988), "Colonoscopic Screening of persons With Suspected Risk Factors for Colon Cancer" *Gastroenterology* 94: 395–400.

Gull Laboratories, Inc. (1996) XTRAX DNA Extraction Kit (Information Sheet), pp. 1–3.

Gyllensten U. B., Allen M., (1995) "Sequencing of In Vitro Amplified DNA," *Recombinant DNA Methodology II,* (Wu, ed.), pp. 565–578.

Hasegawa et al., (1995) "Detection of K-ras Mutations in DNAs Isolated From Feces of Patients with Colorectal Tumors by Mutant-Allele-Specific Amplification (MASA)," *Oncogene*, vol. 10, pp. 1441-1445.

Hoang et al. (1997) "BAT-26, an Indicator of the Replication Error Phenotype in Colorectal Cancers and Cell Lines" *Cancer Research* 57: 300-303.

Honchel et al., (1995) "Genomic Instability in Neoplasia," *Seminars in Cell Biology*, vol. 6, pp. 45-52.

Hoss et al., (Sep. 17, 1992) "Excrement Analysis of PCR" *Scientific Correspondence* pp. 199.

Hunsaker, et al. (1989), "Use of Reversible Target Capture to Detect Subattomole Quantities of Target Nonradioleotopically in Crude Specimens in One Hour," *Abstracts of the 89th Meeting of the American Society for Microbiology*, D-169, p. 110.

Iino et al. (1999) "DNA Microsatellite Instability in Hyperplastic Polyps, Serrated Adenomas, and Mixed Polyps: a Mild Mutator Pathway for Colorectal Cancer?" *Journal of Clinical Pathology* 52: 5-9.

Iniesta et al. (1998) "Genetic Abnormalities and Microsatellite Instability in Colorectal Cancer" *Cancer Detection and Prevention* 22: 383-395.

Ishimaru et al. (1995) "Microsatellite Instability in Primary and Metastatic Colorectal Cancers" *International Journal of Cancer* 64: 153-157.

Jarvinen et al. (1995) "Screening Reduces Colorectal Cancer Rate in Families With Hereditary Nonpolyposis Colorectal Cancer" *Gastroenterology* 108: 1405-1411.

Jernvall et al. (1999) "Microsatellite Instability: Impact on Cancer Progression in Proximal and Distal Colorectal Cancers" *European Journal of Cancer* 35: 197-201.

Jessup J.M. and G.E. Gallick, (Sep./Oct. 1992) "The Biology of Colorectal Carcinoma," *Current Problems in Cancer* pp. 263-328.

Jonsson et al., (Jan. 1995) "From Mutation Mapping to Phenotype Cloning," *Proc. Natl. Acad. Sci.*, vol. 92 pp. 83-85.

Kim et al. (1998) "Microsatellite Instability in Young Patients With Colorectal Cancer" *Pathology International* 48: 586-594.

Konishi et al. (1996) "Molecular Nature of Colon Tumors in Hereditary Nonpolyposis Colon Cancer, Familial Polyposis, and Sporadic Colon Cancer" *Gatroenterology* 111: 307-317.

Morrissey et al., (May 14-18, 1989) "Novel Hybridization Technique with Subattomole Sensitivity in Specimens" *American Society for Microbiology, 89th Annual Meeting*, Abstract D-168, p. 110.

Morrissey, et al., (Sep. 1989) "Nucleic Acid Hybridization Assays Employing dA-Tailed Capture Probes," *Analytical Biochemistry*, vol. 181, No. 2, pp. 345-359.

Morrissey, D. and Mark Collins, (Jun. 1989) "Nucleic Acid Hybridization Assays Employing dA-Tailed Capture Probes. Single Capture Methods," *Mol. And Cell. Probes*, vol. 3, No. 2, pp. 189-207.

Myers, R.M., (Feb. 12, 1993) "The Pluses of Subtraction," *Science*, vol. 259, pp. 942-943.

Naber, S. P., (Dec. 1, 1994) "Molecular Pathology—Detection of Neoplasia," *New England Journal of Medicine*, vol. 331, No. 22, pp. 1508-1510.

Nollau et al., (May 1996) "Isolation of DNA from Stool and Bodily Fluids for PCR Amplication," *BioTechniques*, vol. 20, No. 5, pp. 784-788.

Nollau et al., (1996) "Detection of K-ras Mutations in Stools of Patients with Colorectal Cancer by Mutant-Enriched PCR," *Int. J. Cancer*, vol. 66 pp. 332-336.

Olive, (Feb. 1989) "Detection of Enterotoxigenic *Escherichia coli* after Polymerase Chain Reaction Amplification with a Thermostable DNA Polymerase," *Journal of Clinical Microbiology*, vol. 27, No. 2, pp. 261-265.

Orlow I., et al., (Oct. 18, 1995) "Deletion of the p16 and p15 Genes in Human Bladder Tumors *Journal of the National Cancer Institute*," vol. 87, No. 20, pp. 1524-1529.

Orou, et al., (1995) "Allele-Specific Competitive Blocker PCR: A One-Step Method With Applicability to Pool Screening" *Human Mutation* vol. 6, 163-169.

Paabo et al., (1988) "Mitochondrial DNA Sequences from a 7000-year old Brain," *Nucleic Acids Research*, vol. 16, No. 20, pp. 9775-9777.

Pacek et al., (May 1993) "Determination of Allele Frequencies at Loci with Length Polymorphism by Quantitive Analysis of DNA Amplified from Pooled Samples," *PCR Methods and Applications*, vol. 2, No. 4, pp. 313-317.

Park et al. (1999) "Gene-Environment Interaction in Hereditary Nonpolyposis Colorectal Cancer with Implications for Diagnosis and Genetic Testing" *International Journal of Cancer* 82: 516-519.

Peltomaki et al. (1997) "Mutations Predisposing to Hereditary Nonpolyposis Colorectal Cancer: Database and Results of a Collaborative Study" *Gastroenterology* 113: 1146-1158.

Pharmacia, (1998) *BioDirectory*, pp. 104-109.

Pharmacia, (1991/1992) *Molecular and Cell Biology Catalogue*, pp. 8.3-8.6.

Ahlquist et al., "Colorectal Cancer Screening by Detection of Altered Human DNA in Stool: Feasibility Multitarget Assay Panel," Presented at Digestive Disease Week Annual Conference, Orlando, FL, May 19, 1999 (*Gastroenterology*, 119, pp. 1219-1227(2000)).

Ahlquist et al., "Universal Detection of Aerodigestive Cancers by Assay of Nonapoptotic Human DNA in Stool," Presented at Digestive Disease Week Annual Conference, San Diego, CA, May 2000.

Makristathis et al., "Detection of Helicobacter pylori in Stool Specimens by PCR and Antigen Enzyme Immunoassay," *Journal of Clinical Microbiology*, vol. 36, No. 9, pp. 2772-2774, Sep. 1998.

* cited by examiner

GEL #1

| LANE # | CLINICAL STATUS |
|---|---|
| A | MARKER LANE |
| N | NEGATIVE CONTROL |
| N | NEGATIVE CONTROL |
| 1 | CANCER |
| 2 | NORMAL |
| 3 | CANCER |
| 4 | NORMAL |
| 5 | NORMAL |
| 6 | NORMAL |
| 7 | NORMAL |
| 8 | NORMAL |
| 9 | NORMAL |
| 10 | NORMAL |
| 11 | CANCER |
| 12 | NORMAL |
| 13 | NORMAL |
| 14 | NORMAL |
| 15 | NORMAL |
| N | NEGATIVE CONTROL |
| NA | STANDARD CURVE |
| NA | STANDARD CURVE |
| NA | STANDARD CURVE |
| NA | STANDARD CURVE |
| NA | STANDARD CURVE |
| B | MARKERS |

RESULTS

GEL #2

| LANE # | CLINICAL STATUS |
|---|---|
| A | MARKERS |
| N | NEGATIVE CONTROL |
| N | NEGATIVE CONTROL |
| 16 | NORMAL |
| 17 | NORMAL |
| 18 | CANCER |
| 19 | NORMAL |
| 20 | NORMAL |
| 21 | NORMAL |
| 22 | NORMAL |
| 23 | NORMAL |
| 24 | NORMAL |
| 25 | NORMAL |
| 26 | NORMAL |
| 27 | NORMAL |
| 28 | NORMAL |
| 29 | NORMAL |
| 30 | NORMAL |
| N | NEGATIVE CONTROL |
| NA | STANDARD CURVE |
| NA | STANDARD CURVE |
| NA | STANDARD CURVE |
| NA | STANDARD CURVE |
| NA | STANDARD CURVE |
| B | MARKERS |

RESULTS

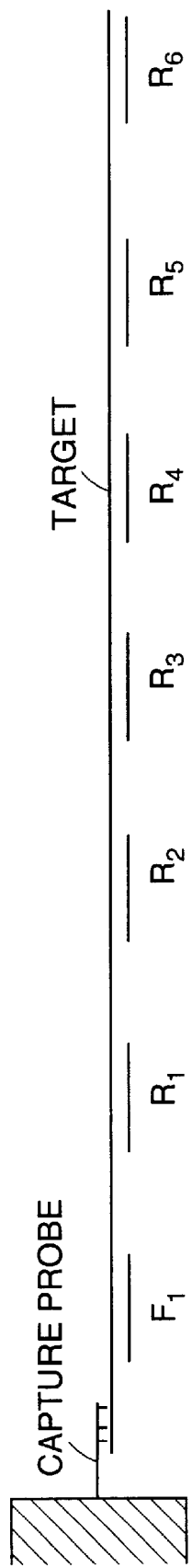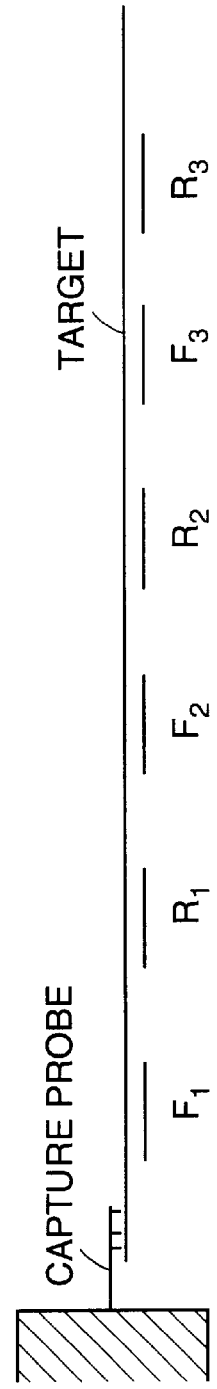

APPARATUS AND METHOD FOR DRUG SCREENING

CROSS-REFERENCE TO RELATED APPLICATIONS

This application is a continuation-in-part of U.S. Ser. No. 09/455,950, filed Dec. 7, 1999, which claims priority to and the benefit of U.S. Ser. No. 60/152,847, filed Sep. 8, 1999. This application also claims priority to and the benefit of U.S. Ser. No. 60/169,457, filed Dec. 7, 1999. All three of these patent applications are incorporated herein by reference.

BACKGROUND OF THE INVENTION

Many diseases are associated with genomic instability. That is, a disruption in genomic stability, such as a mutation, has been linked to the onset or progression of certain diseases. Accordingly, various aspects of genomic instability have been proposed as reliable markers for disease. For example, mutations in the BRCA genes have been proposed as markers for breast cancer, and mutations in the p53 cell cycle regulator gene have been associated with numerous cancers, especially colorectal cancer. It has been suggested that specific mutations might be a basis for molecular screening assays for the early stages of certain types of cancer. See, e.g., Sidransky, et al., Science, 256: 102–105 (1992).

The search for genomic disease markers has been especially intense in the area of cancer detection. Cancer is characterized by uncontrolled cell growth which can be associated with one or more genetic mutations. Such mutations can cause the affected cells to avoid cell death. For example, a mutation in a tumor suppressor gene can cause cells to avoid apoptosis—a type of cell death thought to be under direct genetic control. During apoptosis, cells lose their membranes, the cytoplasm condenses, and nuclear chromatin is split into oligonucleotide fragments of characteristically short length. In fact, those characteristic DNA cleavage patterns have been proposed as an assay for apoptosis.

Once these diseases are detected, the question becomes one of providing the most effective treatment to a patient. Currently, physicians need effective, simple strategies to monitor the efficacy of a drug when administered to a patient. Also, drug developers need a simple, rapid strategy for rational drug design, particularly one that provides results that are predicative of drug activity in vivo.

SUMMARY OF THE INVENTION

The present invention provides screening methods for drug selection and for determining drug activity. Methods of the invention take advantage of the recognition that nucleic acid integrity observed in a tissue or a body fluid sample is a marker for disease, and that preservation of nucleic acid integrity in cellular debris increases with disease severity. According to methods of the invention, nucleic acid integrity also is useful as a marker for use in drug selection and in determining drug efficacy against a wide range of diseases.

As healthy cells proceed through a normal cell cycle, apoptosis or programmed cell death, causes general cellular disruption, including disruption of the cell membrane and degradation of nucleic acids. This process results in small (about 140 bp to about 200 bp) nucleic acid fragments. Diseased cells, such as cancer or pre-cancer cells, lose the ability to undergo apoptosis, and their nucleic acids are not degraded through apoptosis. Nonetheless, a percentage of those cells are sloughed or discarded (e.g., for lack of nutrients, mechanical shearing, etc.), resulting in a population of cells and cellular debris that contain high integrity nucleic acids as well as high integrity proteins, membranes, and other cellular components. That population is subject to lysis and degradation through other mechanisms in the body, but those mechanisms are not able to produce consistently small, low integrity fragments typical of cells that have undergone apoptosis. It was previously recognized that the presence of high integrity cellular components, especially nucleic acids, in a patient sample was a marker for disease. See, e.g., Co-pending, commonly owned U.S. Ser. No. 09/455,950, filed Dec. 7, 1999, which is incorporated by reference herein. It now has been recognized that those same high integrity markers are useful to screen drug candidates for efficacy against diseases, especially cancer and pre-cancer, and to aid in the identification and selection of drugs for use in treating disease. A basis for this recognition is that amounts of high integrity markers fluctuate with disease status. Thus, the efficacy of a drug candidate with respect to a targeted disease is measured by the ability of the drug candidate to reduce disease-associated high integrity markers, such as nucleic acids.

Accordingly, the invention provides methods for screening drug candidates for activity and efficacy that include determining whether a drug candidate produces a decrease in an amount of a high integrity component observed in a patient sample. Preferred high integrity components are nucleic acids or a proteins. Preferred methods of the invention are conducted by obtaining tissue or body fluid sample from a patient having a disease, determining an amount of high integrity nucleic acid present in the sample, treating a patient with a drug candidate, and obtaining a second tissue or body fluid sample to determine whether the amount of high integrity nucleic acid has been reduced. The same method can be carried out on an animal model of a disease.

Methods of the invention also are performed in vitro or ex vivo. For example, the efficacy of a pharmaceutical preparation against disease is measured by its ability to reduce the presence of high integrity nucleic acid directly in a tissue or body fluid sample obtained from a patient known or suspected to have a target disease or an animal model of a disease.

Methods of the invention also are useful to monitor a patient's response to treatment. For example, the efficacy of a treatment is high if that treatment (e.g., administration of a drug candidate or cocktail of drug candidates) produces a decrease in high integrity cellular components observed in post-treatment samples obtained from the patient. As is apparent to the skilled artisan, methods of the invention are useful to screen the efficacy of any treatment means (e.g., drug(s), radiation, diet, surgery, and/or exercise) and are not limited to screening for pharmaceutical activity and efficacy.

Methods of the invention are also useful as in vitro or ex vivo drug candidate screens. In preferred methods, a tissue or body fluid is obtained from a patient or an animal model having a known disease. The sample is screened against one or more candidate drugs by applying the candidate to the sample, or a portion thereof, and observing the effect on nucleic acid integrity in the sample as compared to a pretreatment standard for the disease in question. The standard may be a pretreatment measurement of nucleic acid integrity in the sample or an empirically known standard (e.g., healthy patients). Screening assays of the invention may be multiplexed in order to allow screening of a plurality of intra-patient or inter-patient samples simultaneously. As discussed above, the levels of high integrity nucleic acids are indicative of the disease status of the tissue or body fluid being measured. Accordingly, a drug candidate that is capable of reducing nucleic acid integrity in a sample is a potential medicament effective in treating the disease. In some embodiments the sample is a disease state cell culture.

Preferred patient samples are preferably prepared from specimens likely to contain sloughed cellular debris. Such specimens include, but are not limited to, stool, blood serum or plasma, sputum, pus, and colostrum. Additionally, some specimens do not contain an abundance of intact (non-exfoliated) cells, such as stool, sputum, urine, bile, pancreatic juice, and blood serum or plasma, all of which contain shed cells or cellular debris. Other samples include cerebrospinal fluid, seminal fluid, breast nipple aspirate, and biopsy tissue, but any tissue or body fluid can be used.

As used herein, the term "high integrity nucleic acid" refers to long segments of nucleic acid relative to the length of nucleic acid segments in a normal sample. Those segments typically are greater than about 170 bp, and preferably greater than about 200 bp, in order to exceed the typical length of a fragment resulting from apoptotic degradation. The term "disease state sample" as used herein refers to any sample, whether taken directly from a patient known to have a particular disease, suspected to have a particular disease, or being screened for a particular disease; provided as an animal model or taken from an animal model of a disease; grown as a cell culture that has characteristics of a particular disease or that is diagnostic for or is used as a diagnostic for a particular disease; or harvested from such a cell culture. As used herein, "drug candidate" means a composition of matter that is being investigated for a pharmacological or other activity or that is known to have a pharmacological or other activity, but is being tested to see if it has any type of activity in a particular subject, such as a patient. Efficacy of a drug candidate is one example of a pharmacological activity. Moreover, clinical outcome can be characterized as an activity of a drug candidate.

Nucleic acid is measured by any known means. For example, nucleic acid integrity is measured by the ability to amplify long nucleic acids in the sample. Any nucleic acid locus can be used as a template in an amplification reaction conducted in a tissue sample, fluid sample, or cell culture sample. It is not required that the target genomic loci be associated with any specific disease, because an increase or decrease in amplifiable nucleic acid about any locus is itself diagnostic. If post-treatment amounts of amplification product ("amplicon") are lower than pre-treatment amounts, treatment is said to be effective, and the drug candidate with which the sample was treated is said to be active. It is preferable that, in the case of DNA, the amplification reaction is a polymerase chain reaction ("PCR") or, in the case of RNA, that the amplification reaction is reverse transcriptase PCR. Primers are designed to amplify the locus or loci chosen for analysis.

In some embodiments, a standard amount of amplification product is determined by amplification of a locus, or a portion thereof, being screened in an untreated disease state sample or, alternatively, in a known normal sample (e.g., an intact, wild-type nucleic acid). Also, in certain embodiments, a standard amount is determined by reference to the art. Each amplification reaction in the series is designed to amplify a fragment of a different length. In certain embodiments, the target fragment lengths are about 200 bp, about 400 bp, about 800 bp, about 1.3 Kb, about 1.8 Kb, and about 2.4 Kb. Primers for amplification are designed according to knowledge in the art in order to amplify template, if present, of the desired length at the desired locus. A normal sample, which has undergone or which is undergoing apoptosis, typically contains few or no fragments of significant length. Thus, a series of amplification reactions targeting fragments from about 200 bp to about 2.4 Kb and longer reveals disease state samples that contain nucleic acids that have avoided apoptosis as evidenced by the amplification of large fragments. As such, the efficacy of a drug candidate being used to treat a patient can be assayed by examining the absence or presence of high integrity nucleic acid. Additionally, in vitro or ex vivo disease state samples exhibiting these fragments can be treated with a drug candidate to assess drug candidate activity. A decrease in the number of fragments or the level of fragments present, relative to earlier time course samples or untreated disease state samples, indicates drug candidate activity. That is the case especially when a large (e.g., about 1.8 Kb or about 2.4 Kb) fragment is being screened. Also, the standard amount can be a molecular weight marker on, for example, an electrophoretic gel. Alternatively, methods of the invention can be carried out by hybrid capture. For example, hybrid capture and subsequent analysis of the captured fragments can be used to determine the nucleic acid integrity of a sample.

In an alternative embodiment, screening of drug candidate activity in disease state samples combines detecting amounts of nucleic acid in the sample with an assay for apoptotic cell activity. A positive screen is one that produces both: (1) an amount of nucleic acid that is less than the amount expected to be present in untreated disease state sample, and (2) an amount of apoptotic cell activity that is greater than that expected to be present in a disease state sample. A plurality of genomic loci can be analyzed to determine an amount of amplifiable nucleic acid present at each locus. Analysis across multiple loci using methods of the invention may increase the sensitivity of the screening assay.

In one aspect of the invention, a method for screening drug candidate activity includes the steps of determining a baseline level of high integrity nucleic acid in a first sample that is obtained from a patient having a disease; treating the patient with a drug candidate; and determining whether the high integrity nucleic acid in a second sample that is obtained from the patient is reduced. Typically, high integrity nucleic acid is more than about 200 bp in length. Preferably, the determining steps include amplifying a target nucleic acid to determine the presence of high integrity nucleic acid in the samples. In certain embodiments, the target nucleic acid is amplified with one forward primer and at least two reverse primers. In other embodiments, the target nucleic acid is amplified with at least two pairs of forward and reverse primers. Alternatively and/or in addition to amplification, the determining steps can include capturing the high integrity nucleic acid. In some embodiments, the high integrity nucleic acid is captured on a support-based complementary nucleic acid probe. As noted above, diet, exercise, and radiation are examples of additional, non-pharmacological treatments that can be assessed according to methods of the invention.

Typically, a positive screen is determined by the presence of a lower amount of high integrity nucleic acid in the second sample relative to an amount of high integrity nucleic acid in the first sample. In some embodiments, a positive screen indicates activity of the drug candidate. Also, in some embodiments, a positive screen indicates induction of programmed cell death. Also, in some embodiments, a positive screen indicates induction of apoptotic activity. Examples of samples include stool, sputum, pus, blood serum, blood plasma, urine, saliva, colostrum, bile, and pancreatic juice.

The drug candidate can be any composition of matter, including a nucleic acid, a peptide, and a chemical compound. In some circumstances, the drug candidate is a candidate for an anti-cancer drug. In many instances, activity of a drug candidate is predictive of alleviation of disease symptoms by the drug candidate.

In another aspect of the invention, a kit for screening the activity of a drug candidate includes a first primer that is complementary to a first segment of a target nucleic acid; a second primer that is complementary to a second segment of the target nucleic acid; and a third primer that is complementary to a third segment of the target nucleic. The second segment is located at least about 170 base pairs from the first segment and the third segment is located at least about 170 base pairs from the first segment.

In another aspect of the invention, a method for screening drug candidate activity includes the steps of determining a baseline level of high integrity nucleic acid in a sample from a subject having a disease; treating the sample with a drug candidate; and determining whether high integrity nucleic acid in the sample is reduced. In some embodiments, the subject is an animal model of a disease.

In another aspect of the invention, a method for screening drug candidate activity includes the steps of determining a baseline level of high integrity nucleic acid in a sample from an animal model of a disease; treating the animal model with a drug candidate; and determining whether the high integrity nucleic acid in a second sample obtained from the animal model is reduced.

Other objects and advantages of the invention are apparent upon consideration of the following drawings and detailed description thereof.

DESCRIPTION OF THE DRAWINGS

FIG. 2 shows a schematic representation of the placement of the primers for amplification in a method of the present invention. In this method, a single forward primer, $F_1$, is used in conjunction with a series of reverse primers, $R_1$ to $R_6$, chosen to amplify progressively longer portions of the target.

FIG. 3 shows a schematic representation of the placement of the primers for amplification in a method of the present invention. In this method, a series of forward and reverse primer pairs, $(F_1, R_1)$ to $(F_3, R_3)$, are chosen to amplify portions of the target spaced at intervals along the target.

DETAILED DESCRIPTION OF THE INVENTION

Figure 1A:
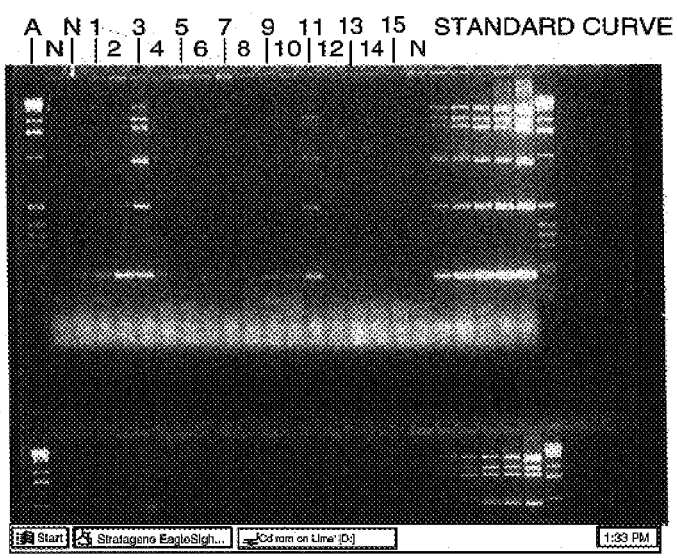
FIGS. 1A and B are gel photographs of results of amplification of DNA in stool from a total of 30 patients and controls. The band intensity relates to the amount of amplifiable DNA in the sample. Lanes N are negative controls, lanes 1, 3, 11, and 18 are results from patients which are indicative of the presence off cancer or adenoma, lanes 2, 4, 5–10, 12–17, and 19–30 are results from patients which are indicative of the absence of cancer or adenoma. The remaining lanes are markers or standards.

The invention provides methods and kits for screening drug activity. Methods of the invention provide information based upon the integrity of nucleic acids in a biological sample. Normal biological samples (those not having indicia of a disease), typically contain cellular debris that includes a majority of short-fragment, low integrity nucleic acids (especially DNA) which are the result of degradation by apoptosis. In a disease state sample, for example, when a mutation has caused genomic instability, the normal cell cycle may be disrupted and apoptotic degradation of nucleic acid and other cellular components may not occur at the rate expected in a normal sample. This situation leads to the presence of high integrity nucleic acid in the disease state sample. Methods of the invention utilize this realization to screen for drug activity.

This screen for drug activity and efficacy can be performed by analyzing samples containing nucleic acid from a patient under treatment with a drug candidate at various time points or by analyzing samples containing nucleic acid from an animal model of a disease treated with a drug candidate. Alternatively, this screen can be performed by treating samples obtained from a patient known or suspected to have a disease, from an animal model of a disease, or from a cell culture representing a disease, in vitro or ex vivo, and analyzing the integrity of nucleic acid in such samples. Drug candidate activity in such systems, typically, provides a lead for rational drug design and/or indicates a likelihood of drug candidate activity in vivo and/or indicates a likelihood of alleviating symptoms of a disease in vivo. Various pharmacological assays can be adapted to methods of the invention. For example, methods of the invention can be used to screen drug candidates on a large scale, used to obtain dose-response data, used for kinetic studies, and used to predict and choose the most effective drug candidate to alleviate a particular patient's symptoms. A variety of kits can be developed based on methods of the invention.

Typically, the nucleic acid being analyzed according to methods of the invention is selected from a coding region of a gene, or a portion thereof, a noncoding nucleic acid region, or a portion thereof, a regulatory element of a gene, or a portion thereof, and/or an unidentified fragment of genomic DNA. In other embodiments, the nucleic acid being interrogated is RNA. As is appreciated by the skilled artisan, any genomic locus is amenable to screening according to the invention. The particular locus or loci chosen for analysis depends, in part, on the disease being screened, the class of drug candidate being screened, and the convenience of the investigator.

As described above, it is not necessary that the locus or loci chosen for analysis be correlated with any specific disease, because any portion of the genome (even those unrelated to disease) may be used in methods of the invention. However, disease-associated loci (those in which a mutation is indicative, causative, or otherwise evidence of a disease) also can be used. Examples of disease-associated loci include p53, apc, MSH-2, dcc, scr, c-myc, B-catnenin, mlh-1, pms-1, pms-2, pol-delta, and bax. In anti-cancer drug candidate screening, the target fragment may optionally be an oncogene, a tumor suppressor, or any other marker associated with cancer. However, it is not necessary to use cancer-associated markers in methods of the invention, as such methods are based on the general recognition that samples indicative of a disease state contain a greater amount of intact nucleic acids and a greater amount of long fragment nucleic acids (generally, high integrity nucleic acids). Accordingly, any convenient target nucleic acid locus may be used in the methods of the invention.

The amount of amplification product may be determined by any suitable or convenient means. Typically, the amount of amplification product is determined by gel electrophoresis. Labels, such as fluorescent or radioactive labels, may be used. The amounts of amplification product produced may be compared to standard amounts by any suitable or convenient means, including, but not limited to visual comparison, machine-driven optical comparison, densitometry, mass spectroscopy, hybrid capture, and other known means. The amplification reaction itself can be any means for amplifying nucleic acid, including, but not limited to, PCR, RT-PCR, OLA, rolling circle, single base extension, and others known in the art. The amplification product can also be measured by signal amplification techniques, such as branch chain amplification (Chiron). Methods of the invention are useful with any platform for the identification, amplification, sequencing, or other manipulation of nucleic acids. For example, methods of the invention can be applied to ligase chain reaction, strand displacement (Becton-Dickinson), and others.

Because many embodiments use amplification of target nucleic acid to assay the level of high integrity nucleic acid in a given sample, generally, the probability that any given set of PCR primers will amplify a DNA fragment having a length exceeding the primer distance is expressed as % of Fragments Amplified=$(FL-PD)/(FL+PD)$ where FL is fragment length (in base pairs) and PD is primer distance (in base pairs). This equation assumes that sample DNA fragment lengths are uniformly distributed (i.e., there is no favored locus at which breaks occur).

After treatment of a patient having or suspected of having a disease, treatment of an animal model for a disease, or treatment of other disease state samples with a drug candidate, nucleic acid sequences of different lengths in a sample are amplified, if present, in order to generate a profile of amplification products indicative of activity of the drug candidate. For example, a sample is exposed to a set of PCR primers. The primers include a single forward primer, which may be a capture probe used to capture target fragments, and a plurality of downstream reverse primers which hybridize to portions of a contiguous sequence (if present) in the sample. Amplifications using these primers will result in a series of amplification products, each having a different length, if the contiguous target sequence is present in the sample. The length of the amplification products are determined by the spacings between the forward primer and each of the downstream reverse primers. An example is shown in FIG. 2, which is a schematic representation showing placement of the primers for amplification.

If the target sequence, or a portion of it, is present in the sample, amplification will result in a series of fragments the length of which is dictated by the spacing of the primers. According to the principles adduced above, a patient, animal model, or other disease state sample treated with an active drug candidate will produce a profile of amplification products in the assay described above that differs from the profile obtained from a disease state sample of an earlier time point during treatment or an untreated disease state sample. A difference that is indicative of drug candidate activity generally is predictive of activity in vivo and/or the ability to alleviate symptoms of a disease in vivo. In one embodiment, the forward primer is designed to hybridize at least about 170 bp upstream, and preferably about 200 bp, upstream of the first reverse primer, and about 2.3 Kb upstream of the last reverse primer. Other reverse primers are designed to hybridize at various locations between the first and last reverse primers. For example, intervals between the forward primer and the various reverse primers can be about 200 bp $(F_1-R_1)$, about 400 bp $(F_1-R_2)$, about 800 bp $(F_1-R_3)$, about 1.3 Kb, $(F_1-R_4)$, about 1.8 Kb $(F_1-R_5)$, and about 2.3 Kb $(F_1-R_6)$. In certain embodiments, the forward primer is at least about 170 bp upstream from a first and second reverse primer. The number and spacing of reverse primers is chosen at the convenience of the skilled artisan.

In some embodiments, a hybrid capture probe is used to anchor a target sequence, preferably on a solid support (e.g., beads). A plurality of probes are then placed at various distances downstream of the capture probe. Those probes can be pairs of forward and reverse primers as discussed above, or they can be signal amplification probes, such as those used in Ligase Chain Reaction (LCR), and others used in the identification of sequences. The plurality of probes hybridize along the length of a target fragment if the target is present in the sample. Thus, by interrogating samples for the presence of the probes, one can determine the integrity of sequences present in the sample. This can be done in numerous ways, including, but not limited to, hybrid capture, PCR, LCR, strand displacement, branched chain, or other assays known in the art that incorporate hybrid probes or primers in order to identify or quantitate sequence. Typically, the capture probe immobilizes a target sequence, if present in the sample. Probes that hybridize to sequence downstream of the capture probe (downstream probes) are placed into each well, such that each downstream probe is spaced a unique distance apart from the common capture probe, and each well contains only one type of downstream probe. Signal is then generated by, for example, amplification, or by standard ELISA procedure followed by amplification, or by LCR, or other methods mentioned above. The presence of signal in each well indicates the presence of sequence of at least the length between the capture probe and the downstream probe. In an alternative embodiment, each well receives multiple different downstream probes, which may be distinctly labeled, and the presence of label(s) is correlated with the length of sequence presence in the sample.

The amplification reactions described above may be conducted according to any suitable or convenient protocol and the fragment size of the resulting amplification products (if any) may be determined by any suitable or convenient means.

In an alternative embodiment, methods of the invention include conducting a series of amplification reactions on a contiguous nucleic acid target fragment, each amplification reaction includes one forward primer and one reverse primer, such that pairs of forward and reverse primers are spaced at intervals on a contiguous fragment suspected to be in the sample. An example of this arrangement is shown in FIG. 3. Preferably, the spacings between each forward and reverse primer pair are equivalent. Also, in some embodiments, the forward primer is about 170 bp to about 200 bp from reverse primer and at least about 170 bp to about 200 bp from a second forward primer. For an untreated disease state sample, the assay described above will result in a series of same-size fragments for most if not all of the primer pairs. Such an array of amplification products evidences a contiguous target sequence indicative of disease (see above). A normal sample should produce little or no amplification product, but in any case will not produce the contiguous array of amplification products expected from a sample containing a relatively intact diagnostic target sequence. Typically, the more activity a drug candidate has, the more like a normal sample the experimental results will appear.

Each of the methods described above are based upon the principle that an intact nucleic acid, or a segment of an intact nucleic acid, in a sample is diagnostic. Thus, variations on the methods described above are contemplated. Such variations include the placement of primers, the number of primers used, the target sequence, the method for identifying sequences, and others. For example, in the method depicted in FIG. 3, and described above, it is not necessary that the numbers of forward and reverse primers be equal. A forward primer may, for example, be used to amplify fragments between two reverse primers. Other variations in primer pair placement are within the skill in the art, as are details of the amplification reactions to be conducted. Finally, as represented in FIGS. 2 and 3, capture probes may be used in methods of the invention in order to isolate a chosen target sequence.

In some embodiments, amplification reactions are conducted on a series of different genomic loci. Preferably, from about 2 to about 7 loci are used. However, the precise number of interrogated loci is determined by the individual investigator based upon the disease to be detected, based upon the class of drug candidate to be used, or based upon convenience. According to methods of the invention, primers are designed to amplify nucleic acid, such as DNA, at each of the chosen loci as described above. A sample from a patient or animal model undergoing treatment with a drug candidate or an in vitro or ex vivo disease state sample, in which at least one locus, preferably at least two loci, and most preferably at least three loci produce(s) reduced levels of detectable high integrity nucleic acid amplification product relative to a first sample taken from a patient earlier in the time course of treating the patient or relative to an untreated disease state sample, is considered a positive drug candidate screen. Additionally, the lengths of fragments to be amplified in this assay may be varied, but are preferably at least about 170 bp each in length. It is not necessary that the same length fragments be amplified at each of the chosen loci, but it is preferred that the same length fragments be amplified at each of the chosen loci.

As described more fully below, patients being treated with a drug candidate can be followed over time. Samples are taken from a patient before treatment begins, and at time points extending over the course of treatment. These samples are analyzed for the integrity of nucleic acid contained within. By monitoring the level of high integrity nucleic acid, a patient's treatment progress can be tracked. This information can be useful, for example, as an early indication of the efficacy of a particular treatment.

If a treatment is effective, these samples will show declining amounts of high integrity nucleic acid. The drug candidate can be administered once, or at intervals, during the treatment period. In one time course the drug candidate can be examined at 2 hours, 4 hours, 6 hours, and 8 hours after the drug treatment has begun. In a longer term time course study the drug candidate can be examined at 48 hours, 1 week, 2 weeks, and 4 weeks after the drug treatment has begun. In comparison to earlier time point samples, the total amount of amplified high integrity nucleic acid (or amplifiable high integrity nucleic acid) detected in later time point samples is expected to be lower if the drug candidates are active or effective in a patient. Conversely, the total amount of amplified high integrity nucleic acid (or amplifiable high integrity nucleic acid) detected in later time point samples is expected to be similar or slightly lower if the drug candidates are inactive or ineffective. Alternatively, the pattern of fragments amplified from high integrity nucleic acid can be analyzed. Fewer fragments (particularly the longer fragments) are expected to be present and/or a lesser amount of some or all of the fragments are expected to be present in a later time course samples as compared to those present in earlier time course samples in a patient being treated with an active or effective drug candidate. The fragments will remain the same, increase in number and/or amount (e.g., band intensity), or will slightly diminish in number and/or amount in later time course samples as compared with earlier time course sample in a patient being treated with an inactive or ineffective drug candidate.

These same principals can be applied to a drug screen using animal models for a particular disease state. The integrity of nucleic acid in samples taken from the animal model being treated with a drug candidate is monitored over time and activity is assessed as described above.

Alternatively, methods of the invention for screening drugs, in an in vitro setting, allow for one or a multitude of compounds (e.g., simultaneously) to be screened for activity. A disease state sample is placed into an experimental container, such as a wells of a multi-well sample plate. The sample is exposed to one or more compounds and analyzed for its content of high integrity nucleic acid. In comparison to an untreated disease state sample, the total amount of amplified high integrity nucleic acid (or amplifiable high integrity nucleic acid) is expected to be lower in samples treated with active drug candidates, and the total amount of amplified high integrity nucleic acid (or amplifiable high integrity nucleic acid) will be similar, increased, or slightly lower in samples treated with inactive drug candidates. Alternatively, the pattern of fragments amplified from high integrity nucleic acid can be analyzed. Fewer fragments (particularly the longer fragments) are expected to be present and/or a lesser amount of some or all of the fragments are expected to be present in a sample treated with an active drug candidate as compared to those present in an untreated sample. The fragments will remain the same, will increase, or will slightly diminish in number or amount (e.g., band intensity) in samples treated with an inactive drug candidate.

If a drug candidate is known to be active, or if it is screened and determined to be active, a dose-response curve can be generated. By applying increasing dosages of the drug candidate to disease state samples, such as, but without limitation, animal models and tissue cultures, and analyzing the level of high integrity nucleic acid (amplified or amplifiable) at each dosage, a curve can be drawn relating drug candidate dosage to activity (as measured by the level of high integrity nucleic acid). These two basic pharmacological techniques are exemplary, and not meant to be limiting. However, these techniques do provide a way to rapidly screen for active drug candidates as well as make a determination of their potency. For example, but without limitation, anti-cancer or anti-bowel inflammation drug candidates can be screened.

Alternatively, the drug activity can be assayed ex vivo. In one embodiment, tissue or fluid can be removed from a patient prior to treatment. This sample can be treated with various drug candidates that might be expected to alleviate the symptoms of a disease. Activity is assayed as described above. A drug candidate showing the most activity for the sample can be chosen as a drug candidate that is likely to alleviate symptoms of a disease in the patient from which the sample was taken. In another embodiment tissue is removed from an animal model and is treated with a drug candidate. Activity is assessed as described above and can be used to screen drug candidates.

Methods of the invention also can be used to screen or to "qualify" samples for further analysis (e.g., genetic, biochemical, cytological, or other analyses). The sample to be qualified is examined for the presence of high integrity nucleic acid, and, if present, the high integrity nucleic acid indicates that a sample likely can be used as a sample for in vitro, ex vivo (for example, when qualifying an animal model) screening, or in vivo animal model screening. Thus, disease state samples that provide the basis of drug candidate activity screening can be chosen according to this method. Some of the diseases for which samples are qualified, and for which methods of the invention can detect changes in the integrity of nucleic acid, include, but are not limited to, colon cancers and adenomas; lymphomas; and stomach, lung, liver, pancreas, prostate, kidney, testicular, bladder, uterus, or ovarian cancers or adenomas. Additionally, diseases such as inflammatory bowel syndrome, inflammatory bowel disease, Crohn's disease, and others, in which a genomic instability is thought to play a role, can be examined. Moreover, the profile of amplifiable DNA in a sample is correlated with proteins that have been associated with disease. For example, up regulation of the apoptosis protein, survivin, is correlated with increased amounts of amplifiable DNA, as is the Ras oncogene, as well as other oncogenes and their gene products.

Methods of the invention also are useful as assays for apoptosis. The presence of amplified fragments of high integrity nucleic acid or large quantities of high integrity nucleic acid in a sample indicates that the sample was derived from cells that did not proceed through apoptosis. The absence of such fragments or quantities indicates that cells that contributed to the sample underwent apoptosis. Accordingly, an apoptotic activity assay of the invention, either alone or in combination with other assays for genomic instability, also are useful as screens for disease. Moreover, programmed cell death is measured in a similar way to apoptotic activity, with the induction of programmed cell death being correlated with an increase in apoptotic activity in many systems.

The following examples provide further details of methods according to the invention. Accordingly, while exemplified in the following manner, the invention is not so limited and the skilled artisan will appreciate its wide range of application upon consideration thereof.

Exemplary Method for the Detection of Colon Cancer

The following example relates to screening for colon cancer in voided stool samples. Based upon the principles upon which the invention is based (see above), the same analysis can be performed on other samples, such as those mentioned above, with the same results as shown herein.

For the analysis of stool samples, preferred methods of the invention comprise obtaining at least a cross-sectional or circumferential portion of a voided stool as taught in U.S. Pat. No. 5,741,650, and co-pending, co-owned U.S. Pat. No. 5,952,178, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA). However, as taught in co-pending, co-owned U.S. patent application Ser. No. 09/491,093, incorporated by reference herein, it has been discovered that the use of at least 150 mM EDTA greatly improves the yield of nucleic acid from stool. Thus, a preferred buffer for stool homogenization includes phosphate buffered saline, 20–100 mM NaCl or KCl, at least 150 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed. Total DNA is isolated using techniques known in the art.

Screening Assay Protocol

The size of human DNA fragments obtained above can be determined by numerous means. For example, human DNA can be separated using gel electrophoresis. A 3% agarose gel is prepared using techniques known in the art. See Ausubel et al., Short Protocols in Molecular Biology, John Wiley & Sons, 1195, pgs. 2-23–2-24, incorporated by reference herein. The size of human DNA fragments is then determined by comparison to known standards. Fragments greater than about 200 bp provide a positive screen. While a diagnosis can be made on the basis of the screen alone, patients presenting a positive screen are preferably advised to seek follow-up testing to render a confirmed diagnosis.

A preferred means for determining human DNA fragment length uses PCR. Methods for implementing PCR are well-known. In the present invention, human DNA fragments are amplified using human-specific primers. Amplicon of greater than about 200 bp produced by PCR represents a positive screen. Other amplification reactions and modifications of PCR, such as ligase chain reaction, reverse-phase PCR, Q-PCR, and others may be used to produce detectable levels of amplicon. Amplicon may be detected by coupling to a reporter (e.g., fluorescence, radioisotopes, and the like), by sequencing, by gel electrophoresis, by mass spectrometry, or by any other means known in the art, as long as the length, weight, or other characteristic of the amplicons identifies them by size.

EXAMPLES

Experiments are described below that determine if a drug candidate treatment is active and effective by analyzing the integrity of nucleic acid in various samples taken from patients and animal models of disease. These examples are illustrative of the invention and are not meant to be limiting.

Example 1

An experiment is conducted to determine treatment outcome over time in cancer or adenoma patients. Stool samples are obtained and frozen, and DNA is isolated. The samples are screened by hybrid capturing human DNA and determining the amount of amplifiable DNA having at least 200 base pairs. Each frozen stool specimen, weighing from 7–33 grams, is thawed and homogenized in 500 mM Tris, 16 mM EDTA, and 10 mM NaCl, pH 9.0 at a volume to mass ratio of 3:1. Samples are then rehomogenized in the same buffer to a final volume to mass ratio of 20:1 and spun in glass macro beads at 2356×g. The supernatant is collected and treated with SDS and proteinase k. The DNA is then phenol-chloroform extracted and precipitated with alcohol. The precipitate is suspended in 10 mM Tris and 1 mM EDTA (1×TE), pH 7.4. Finally, the DNA is treated with RNase.

Prior to amplification, DNA is isolated from the samples by hybrid capture. Biotynilated probes against portions of the BRCA1, BRCA2, p53, APC genes are used.

The BRCA1 probe is
5'GATTCTGAAGAACCAACTTTGTCCTTAACT-AGCTCTT3' (SEQ ID NO:8).

The BRCA2 probe is
5'CTAAGTTTGAATCCATGCTTTGCTCTTCTTGAT-TATT3' (SEQ ID NO:9).

The APC1 probe is
5'CAGATAGCCCTGGACAAACCATGCCAC-CAAGCAGAAG3' (SEQ ID NO:10).

The p53 probe, hybridizing to a portion of exon 5, is
5'TACTCCCCTGCCCTCAACAAGATGTTTTGCCA-ACTGG3' (SEQ ID NO:4).

The APC2 probe is
5'GAAGTTCCTGGATTTTCTGTTGCTGGATGGT-AGTTGC3' (SEQ ID NO:11).

A 300 µl aliquot of sample is placed in 300 µl of 6 M guanidine isothiocyanate buffer with 10 µl of each capture probe, and incubated overnight at 25 C. Captured DNA is isolated using 100 µl capture beads incubated for one hour at room temperature. The DNA is eluted off the beads and PCR amplified under standard PCR conditions.

Figure 1B:
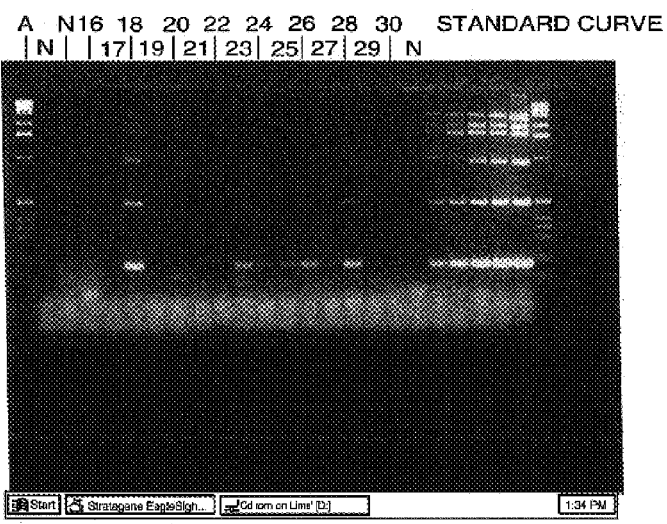

According to methods of the invention, amplification reactions are conducted using forward and reverse primers through the 5 loci for each sample. Forward and reverse primers are spaced to amplify fragments of 200 bp, 400 bp, 800 bp, 1.3 Kb, 1.8 Kb, and 2.4 Kb. Each of 30 PCR reactions is run for 36 cycles. Amplicon is run on a 3% Seakeam gel, and stained with ethidium bromide. The results are shown in FIGS. 1A and 1B. Each figure represents the results for 15 of the 30 patients.

As shown in those figures, patients with cancer or adenoma have an increased yield of amplifiable DNA. That is especially true at the 1.8 Kb level and above. Thus, patients with cancer or adenoma not only produce more amplifiable DNA in their stool, but also produce larger DNA fragments than are produced in the stool of patients who do not have cancer. Thus, both an increased yield of amplifiable DNA and the presence of high molecular weight DNA, especially that at 1.8 Kb and above, are indicative of patient disease status.

Those patients (lanes 1, 3, 11, and 18) that have high integrity nucleic acid are treated with an anti-cancer drug candidate. The patients are given a dose of the drug candidate at intervals dictated by the pharmacokinetics exhibited by the drug candidate being administered, and other factors that are known to those skilled in the art. The patients are treated and monitored over a period of a month. Samples are taken from each patient for analysis at 48 hours, 1 week, 2 weeks and 4 weeks. Patients that do not have high integrity nucleic acid (i.e., normals) are either excluded from treatment and analysis (for example, in the case where only patients that are diagnosed with cancer are treated with a drug candidate known to have efficacy as an anti-cancer drug) or are included in subsequent monitoring and given a placebo treatment (for example, in a clinical study relating to the efficacy of a drug candidate). In this example, the patients without high integrity nucleic acid are excluded from treatment, and the patients having high integrity nucleic acid are treated.

The hypothetical expected results obtained at the locus interrogated with BCRA1, for each of the four patients having high integrity nucleic acid, are presented in Table 1, below. Similar hypothetical results are expected at the other loci being interrogated, because integrity of nucleic acid is predictive notwithstanding the loci being interrogated.

TABLE 1

Hypothetical expected results at the BCRA1 locus.

| | Sample taken at 48 Hours | Sample taken at 1 Week | Sample taken at 2 Weeks | Sample taken at 4 Weeks |
|---|---|---|---|---|
| Patient 1 | Bands greater than 800 bp contain less nucleic acid than in initial sample | Bands greater than 800 bp missing | Bands between 200 bp and 800 bp contain less nucleic acid than in initial sample | Mainly a band at 200 bp |
| Patient 2 | No difference from initial sample | No difference from initial sample | No difference from initial sample | No difference from initial sample |
| Patient 3 | Bands greater than 800 bp contain less nucleic acid than in initial sample | Bands greater than 800 bp missing | Bands between 200 bp and 800 bp contain less nucleic acid than in initial sample | Mainly a band at 200 bp |
| Patient 4 | No difference from initial sample | Bands greater than 800 bp contain less nucleic acid than in initial sample | Bands greater than 800 bp contain less nucleic acid than in initial sample | Bands between 200 bp and 800 bp contain less nucleic acid than in initial sample |

As can be seen in the results above, patients 1 and 3 responded favorably to the drug treatment. By the end of the 4 week monitoring period, these patients have a profile of nucleic acid integrity more similar to that of a normal than to an untreated disease state. During the monitoring period, bands representing the longest fragments being amplified were absent first, followed by bands representing shorter fragments being amplified (but still greater than 200 bp). Patient 4 showed some response to the drug treatment, but not as great as that for patients 1 and 3. During the monitoring period of patient 4, the longest fragments were absent after 2 weeks as compared to 1 week for patients 1 and 3. The shorter fragments being amplified, between 200 bp and 800 bp, were not absent at the end of the 4 week monitoring period, but, rather were only reduced relative to the initial measurement. This result could indicate, for example, that the treatment was only partially effective in treating the patient's cancer or that the treatment takes longer to become effective in the patient. Finally, patient 2 showed no decrease in the amount of any length fragment, indicating that the drug candidate had no effect on patient 2.

Example 2

Another experiment is conducted to determine treatment outcome over time in cancer or adenoma patients utilizing several loci that are different from those used in Example 1. Stool samples were collected from 9 patients who presented with symptoms or a medical history that indicated that a colonoscopy should be performed. Each stool sample was frozen. Immediately after providing a stool sample, each patient was given a colonoscopy in order to determine the patient's disease status. Based upon the colonoscopy results, and subsequent histological analysis of biopsy samples taken during colonoscopy, individuals were placed into one of two groups: normal or abnormal. The abnormal group consisted of patients with cancer or with an adenoma of at least 1 cm in diameter. Based upon these results, 4 of the 9 patients were placed into the abnormal group. Samples from the abnormal group are analyzed further, and the normals are not further analyzed.

The samples are screened by hybrid capturing human DNA, and determining the amount of amplifiable DNA having at least 200 base pairs. Each frozen stool specimen, weighing from 7–33 grams, is thawed and homogenized in 500 mM Tris, 16 mM EDTA, and 10 mM NaCl, pH 9.0 at a volume, to mass ratio of 3:1. Samples are then rehomogenized in the same buffer to a final volume-to-mass ratio of 20:1, and spun in glass macro beads at 2356×g. The supernatant is collected and treated with SDS and proteinase k. The DNA is then phenol-chloroform extracted and precipitated with alcohol. The precipitate is suspended in 10 mM Tris and 1 mM EDTA (1×TE), pH 7.4. Finally, the DNA is treated with RNase.

Human DNA is isolated from the precipitate by sequence-specific hybrid capture. Biotynilated probes against portions of the p53, K-ras, and apc genes are used.

The K-ras probe was 5'GTGGAGTATTTGATAGTGTAT-TAACCTTATGTGTGAC 3' (SEQ ID NO: 1).

There were two apc probes: apc-1309 was 5'TTCCAG-CAGTGTCACAGCACCCTAGAACCAAATCCAG 3' (SEQ ID NO: 2), and apc-1378 was 5'CAGATAGCCCTG-GACAAACAATGCCACGAAGCAGAAG 3' (SEQ ID NO: 3).

There were four probes against p53, the first (hybridizing to a portion of exon 5) was 5'TACTCCCCTGCCCTCAA-CAAGATGTTTTGCCAACTGG3' (SEQ ID NO:4), the second (hybridizing to a portion of exon 7) was 5'ATTTCT-TCCATACTACTACCCATCGACCTCTCATC3' (SEQ ID NO: 5), the third, also hybridizing to a portion of exon 7 was 5'ATGAGGCCAGTGCGCCTTGGGGAGACCT-GTGGCAAGC3' (SEQ ID NO: 6); and finally, a probe against exon 8 had the sequence 5'GAAAGGA-CAAGGGTGGTTGGGAGTAGATGGAGCCTGG3' (SEQ ID NO: 7).

A 10 µl aliquot of each probe (20 pmol/capture) is added to a suspension containing 300 µl DNA in the presence of 310 µl 6M GITC buffer for 2 hours at room temperature. Hybrid complexes are isolated using streptavidin-coated beads (Dynal). After washing, probe-bead complexes are suspended at 25° C. for 1 hour in 0.1×TE buffer, pH7.4. The suspension is then heated for 4 minutes at 85° C., and the beads are removed.

Captured DNA is then amplified using PCR, essentially as described in U.S. Pat. No. 4,683,202, incorporated by reference herein. Each sample is amplified using forward and reverse primers through 7 loci (Kras, exon 1, APC exon 15 (3 separate loci), p53, exon 5, p53, exon 7, and p53, exon 8) in duplicate (for a total of 14 amplifications for each locus). Seven separate PCRs (40 cycles each) are run in duplicate using primers directed to detect fragments in the sample having 200 base pairs or more. Amplified DNA is placed on a 4% Nusieve (FMC Biochemical) gel (3% Nusieve, 1% agarose), and stained with ethidium bromide (0.5 µg/ml). The resulting amplified DNA is graded based upon the relative intensity of the stained gels. Seven different loci that are amplified. All four abnormal patients have amplifiable DNA of 200 bp or greater in length. The results are the same regardless of which locus was amplified.

The four abnormal patients are then treated with a drug candidate for a period of four weeks. As shown in Table 2, below, a similar result to that in Example 1 is obtained for these four patients.

TABLE 2

| | | Hypothetical expected results at the K-ras locus. | | | |
|---|---|---|---|---|---|
| | | Sample taken at 48 Hours | Sample taken at 1 Week | Sample taken at 2 Weeks | Sample taken at 4 Weeks |
| | Patient 1 | Bands greater than 800 bp contain less nucleic acid than in initial sample | Bands greater than 800 bp missing | Bands between 200 bp and 800 bp contain less nucleic acid than in initial sample | Mainly a band at 200 bp |
| | Patient 2 | No difference from initial sample | No difference from initial sample | No difference from initial sample | No difference from initial sample |
| | Patient 3 | Bands greater than 800 bp contain less nucleic acid than in initial sample | Bands greater than 800 bp missing | Bands between 200 bp and 800 bp contain less nucleic acid than in initial sample | Mainly a band at 200 bp |

TABLE 2-continued

Hypothetical expected results at the K-ras locus.

| | Sample taken at 48 Hours | Sample taken at 1 Week | Sample taken at 2 Weeks | Sample taken at 4 Weeks |
|---|---|---|---|---|
| Patient 4 | No difference from initial sample | Bands greater than 800 bp contain less nucleic acid than in initial sample | Bands greater than 800 bp contain less nucleic acid than in initial sample | Bands between 200 bp and 800 bp contain less nucleic acid than in initial sample |

Example 3

In this example, methods of the invention are used in patients who had a colorectal adenoma or colorectal cancer. A stool sample is obtained from each of these patients and prepared, as described above. Fragments of the 5 different loci referred to in Example 1 are amplified using primers spaced 200, 400, 800, 1300, 1800, and 2400 base pairs apart using the protocol described above in Example 1. Each amplification is scored such that successful amplification of a fragment receives a score of 1, and no amplification receives a score of 0. Because five loci were interrogated using 6 primer pairs each, the maximum score is 30 (successful amplification of all 6 fragments at all five loci). The cutoff for a positive screen is set at 21. The results are shown below. Tables 3 and 4 indicate which patients are positive for an adenoma or a carcinoma based upon this scoring system.

TABLE 3

Scoring for patients to determine if patients have an adenoma.

| Patient No. | Age | Score |
|---|---|---|
| P-003 | | 29 |
| P-001 | | 23 |
| P-045 | | 22 |
| P-162 | | 21 |
| P-163 | | 16 |
| P-088 | | 15 |
| P-050 | | 13 |
| P-060 | | 11 |
| P-061 | | 11 |
| P1058 | | 10 |
| P-075 | | 10 |
| P-077 | | 8 |
| P-024 | | 7 |
| P-056 | | 7 |
| P-067 | | 7 |
| P-025 | | 6 |
| P-080 | | 4 |
| P-123 | | 4 |
| P-048 | | 3 |
| P-040 | | 2 |
| P-006 | | 1 |
| P-004 | | 0 |
| P-015 | | 0 |
| P-083 | | 0 |
| P-047 | | |
| P-129 | | |

TABLE 4

Scoring for patients to determine if patients have a carcinoma.

| Patient No. | Age | Score |
|---|---|---|
| P-064 | | 30 |
| P-103 | | 30 |

TABLE 4-continued

Scoring for patients to determine if patients have a carcinoma.

| Patient No. | Age | Score |
|---|---|---|
| P-104 | | 30 |
| P-108 | | 30 |
| P-101 | | 29 |
| P-102 | | 29 |
| P-099 | | 28 |
| P-107 | | 28 |
| P-110 | | 26 |
| P-098 | | 25 |
| P-134 | | 24 |
| P-062 | | 23 |
| P-090 | | 23 |
| P-095 | | 23 |
| P-093 | | 22 |
| P-100 | | 21 |
| P-122 | | 18 |
| P-084 | | 15 |
| P-109 | | 15 |
| P-118 | | 10 |
| P-138 | | 10 |
| P-091 | | 8 |
| P-096 | | 8 |
| P-053 | | 7 |
| P-119 | | 6 |
| P-117 | | 5 |
| P-105 | | 0 |
| P-097 | | |

Those with a score of 21 or higher are treated with an anti-cancer drug candidate and monitored as described for Example 1. The hypothetical expected results of treatment are presented in Tables 5 and 6 below.

TABLE 5

Hypothetical expected results for patients with an adenoma during treatment, with scoring at all five loci.

| | Score of Sample Taken at 48 Hours | Score of Sample Taken at 1 Week | Score of Sample Taken at 2 Weeks | Score of Sample Taken at 4 Weeks |
|---|---|---|---|---|
| P-003 | 28 | 24 | 20 | 14 |
| P-001 | 23 | 23 | 23 | 23 |
| P-045 | 22 | 20 | 14 | 12 |
| P-162 | 21 | 20 | 18 | 16 |

TABLE 6

Hypothetical expected results for patients with a carcinoma during treatment, with scoring at all five loci.

| | Score of Sample Taken at 48 Hours | Score of Sample Taken at 1 Week | Score of Sample Taken at 2 Weeks | Score of Sample Taken at 4 Weeks |
|---|---|---|---|---|
| P-064 | 29 | 27 | 20 | 16 |
| P-103 | 29 | 28 | 21 | 15 |
| P-104 | 30 | 27 | 19 | 14 |
| P-108 | 29 | 29 | 25 | 24 |
| P-101 | 28 | 22 | 16 | 9 |
| P-102 | 28 | 25 | 20 | 23 |
| P-099 | 27 | 23 | 19 | 12 |
| P-107 | 28 | 28 | 28 | 28 |
| P-110 | 26 | 25 | 20 | 17 |
| P-098 | 25 | 20 | 15 | 8 |
| P-134 | 23 | 19 | 17 | 15 |
| P-062 | 23 | 21 | 16 | 14 |
| P-090 | 23 | 20 | 15 | 14 |
| P-095 | 22 | 21 | 16 | 12 |
| P-093 | 21 | 19 | 18 | 17 |
| P-100 | 21 | 21 | 21 | 21 |

The score of the patients, which reflects successful amplification of a fragment, which, in turn, reflects the level of high integrity nucleic acid, as described above, is shown for a time course of treatment with an anti-cancer drug candidate in Tables 5 and 6. Because the cut-off for a positive screen for a diseased patient is set to 21, when the score of a patient drops below 21, the drug treatment is considered effective. As shown in Tables 5 and 6, the length of time it takes for a score to drop below 21 varies from patient to patient, and the magnitude of the change also varies. Some patients do not respond to treatment, as indicated by a score that does not drop below 21 or by a score that does not change at all.

Example 4

This example shows how methods of the invention can screen drug candidates for activity in an animal (non-human) model of a disease ("diseased animal") using the presence or absence of amplifiable high integrity nucleic acid as a marker for activity. Such an experiment can provide leads for drug development and/or predict which compounds are likely to be active in vivo and/or predict which compounds are likely to alleviate symptoms of a disease in vivo.

An animal model of a disease is used as the test subject, and a normal animal is used as a control. Because the assay is to be conducted in triplicate, for each drug candidate to be tested, three diseased animals are treated with the drug candidate. As controls, a diseased animal is treated with a sham treatment, such as the carrier in which the drug candidate is suspended for administration; a normal animal is treated with the sham treatment; and a normal animal is treated with the drug candidate.

The animals are given these treatments periodically over a period of three weeks. During the administration period, samples are taken from the animals, the samples are prepared, and the samples are analyzed for nucleic acid integrity, as described above. Samples are taken at a time before treatment, at 48 hours post-treatment, 1 week post-treatment, 2 weeks post-treatment, and 3 weeks post-treatment. Analysis is accomplished as described above. Briefly, DNA is extracted from these samples. PCR is used to amplify the extracted DNA about a locus suspected to be associated with the disease. One forward primer is used with six reverse primers. The forward primer is separated from each reverse primer by 200 bp ($F_1$–$R_1$), 400 bp ($F_1$–$R_2$), 800 bp ($F_1$–$R_3$), 1.3 Kb, ($F_1$–$R_4$), 1.8 Kb ($F_1$–$R_5$), and 2.3 Kb ($F_1$–$R_6$). After amplification, the PCR product is run out on a separation gel.

At the endpoint (3 weeks), the untreated diseased animal (sham treatment) is expected to show bands for fragments (amplified high integrity nucleic acid) at most, if not all, of the primer pairs (200 bp ($F_1$–$R_1$), 400 bp ($F_1$–$R_2$), 800 bp ($F_1$–$R_3$), 1.3 Kb, ($F_1$–$R_4$), 1.8 Kb and 2.3 Kb ($F_1$–$R_6$)). The normal animal treated with the sham treatment is expected to show very little, if any, amplified high integrity nucleic acid. Thus, bands corresponding to fragments of 400 bp ($F_1$–$R_2$), 800 bp ($F_1$–$R_3$), 1.3 Kb, ($F_1$–$R_4$), 1.8 Kb ($F_1$–$R_5$), and 2.3 Kb ($F_1$–$R_6$) are expected to be substantially absent in the untreated normal sample. More particularly, a very light band, or no band at all, is expected for the 200 bp fragment ($F_1$–$R_1$), and no other bands, especially those corresponding to longer fragments, are expected. A similar pattern is expected for the normal animal treated with the drug candidate.

In this case, the pattern of bands, representing the fragments amplified with the various primer pairs, is used as the marker of high integrity nucleic acid, and, thus, drug candidate activity. If the drug candidate has activity, the profile of amplified high integrity nucleic acid from a treated diseased animal sample will be different from that of the untreated diseased animal sample. More particularly, if the drug candidate has an activity, fewer bands and/or lighter bands from a treated diseased animal sample will be seen relative to the untreated diseased animal sample. The stronger the activity of the drug candidate, the fewer the bands that will be seen and/or the lighter the bands that will be seen. It is expected that the most powerfully active drug candidates will produce a band pattern similar to that of the normal animal sample. Moreover, during the time course of the experiment, samples taken from the diseased animal over the time course will show changes in the number and/or level of intensity of the bands that are seen, if the drug candidate is active. Hypothetical expected results are shown in Table 7, below.

TABLE 7

Hypothetical expected results at the amplified target.

| | | Sample taken at 48 Hours | Sample taken at 1 Week | Sample taken at 2 Weeks | Sample taken at 3 Weeks |
|---|---|---|---|---|---|
| | Diseased Animal 1 | Bands greater than 800 bp contain less nucleic acid than in initial sample | Bands greater than 800 bp missing | Bands between 200 bp and 800 bp contain less nucleic acid than in initial sample | Mainly a band at 200 bp |

TABLE 7-continued

Hypothetical expected results at the amplified target.

| | Sample taken at 48 Hours | Sample taken at 1 Week | Sample taken at 2 Weeks | Sample taken at 3 Weeks |
|---|---|---|---|---|
| Diseased Animal 2 | No difference from initial sample | Bands greater than 800 bp contain less nucleic acid than in initial sample | Bands greater than 800 bp contain less nucleic acid than in initial sample | Bands between 200 bp and 800 bp contain less nucleic acid than in initial sample |
| Diseased Animal 3 | Bands greater than 800 bp contain less nucleic acid than in initial sample | Bands greater than 800 bp missing | Bands between 200 bp and 800 bp contain less nucleic acid than in initial sample | Mainly a band at 200 bp |
| Untreated Diseased Animal | No difference from initial sample (presence of high integrity nucleic acid) | No difference from initial sample (presence of high integrity nucleic acid) | No difference from initial sample (presence of high integrity nucleic acid) | No difference from initial sample (presence of high integrity nucleic acid) |
| Untreated Normal Animal | No difference from initial sample (no high integrity nucleic acid) | No difference from initial sample (no high integrity nucleic acid) | No difference from initial sample (no high integrity nucleic acid) | No difference from initial sample (no high integrity nucleic acid) |
| Treated Normal Animal | No difference from initial sample (no high integrity nucleic acid) | No difference from initial sample (no high integrity nucleic acid) | No difference from initial sample (no high integrity nucleic acid) | No difference from initial sample (no high integrity nucleic acid) |

Drug candidates that are promising can be studied further. For example, the same experiment can be run by treating diseased animals with various doses of a particular drug candidate, and comparing the pattern of amplified fragments from the treated diseased animal samples with an untreated diseased animal sample and with normal animal samples, as described above. A dose-response curve can be constructed to represent the effects of drug candidate dosage on drug candidate activity.

Example 5

This example shows how methods of the invention can screen compounds that induce apoptotic activity or programmed cell death using the presence or absence of amplifiable high integrity nucleic acid as a marker. Essentially, these experiments are carried out the same way as in Example 4, and a similar endpoint to that in Example 4 is examined to determine if an induction of apoptotic activity or programmed cell death has occurred. If the compound induces apoptotic activity and/or programmed cell death, the profile of amplified high integrity nucleic acid in a sample from a treated diseased (or normal) animal will be different from that of the untreated diseased (or normal) animal sample. If the compound induces apoptotic activity and/or programmed cell death, fewer bands and/or lighter bands will be seen in a sample from a treated diseased (or normal) animal relative to the untreated diseased (or normal) animal sample. The more induction of apoptotic activity and/or programmed cell death, the fewer the bands that will be seen and/or the lighter the bands that will be seen.

Example 6

This example shows how methods of the invention can screen drug candidates for activity in a specimen taken from an animal model (non-human) of a disease ("diseased animal") using the presence or absence of amplifiable high integrity nucleic acid as a marker for activity. Such an experiment can provide leads for drug development and/or predict which compounds are likely to be active in vivo and/or predict which compounds are like to alleviate symptoms of a disease in vivo.

An animal model of a disease is used as the test subject, and a normal animal is used as a control. Because the assay is to be conducted in triplicate, for each drug candidate to be tested, a tissue specimen from each of three diseased animals is removed and each specimen is treated with the drug candidate. As controls, a tissue specimen from a diseased animal is treated with a sham treatment, such as the carrier in which the drug candidate is suspended; a tissue specimen from a normal animal is treated with the sham treatment; and a tissue specimen from a normal animal is treated with the drug candidate.

The tissue specimens are cultured and are given these treatments as a bolus dose and incubated for 8 hours. During the 8 hour incubation period, samples are taken from the cultured specimens, the samples are prepared, and the samples are analyzed for nucleic acid integrity, as described above. Samples are taken at a time before treatment, at 2 hours post-treatment, 4 hours post-treatment, 6 hours post-treatment, and 8 hours post-treatment. Analysis is accomplished as described above. Briefly, DNA is extracted from these samples. PCR is used to amplify the extracted DNA about a locus suspected to be associated with the disease. One forward primer is used with six reverse primers. The forward primer is separated from each reverse primer by 200 bp ($F_1$–$R_1$), 400 bp ($F_1$–$R_2$), 800 bp ($F_1$–$R_3$), 1.3 Kb, ($F_1$–$R_4$), 1.8 Kb ($F_1$–$R_5$), and 2.3 Kb ($F_1$–$R_6$). After amplification, the PCR product is run out on a separation gel.

At the endpoint (8 hours), samples from the untreated tissue specimen from the diseased animal (sham treatment) are expected to show bands for fragments (amplified high integrity nucleic acid) at most, if not all, of the primer pairs (200 bp ($F_1$–$R_1$), 400 bp ($F_1$–$R_2$), 800 bp ($F_1$–$R_3$), 1.3 Kb, ($F_1$–$R_4$), 1.8 Kb ($F_1$–$R_5$), and 2.3 Kb ($F_1$–$R_6$)). Samples from the tissue specimen, that are treated with the sham treatment, taken from the normal animal are expected to show very little, if any, amplified high integrity nucleic acid. Thus, bands corresponding to fragments of 400 bp ($F_1$–$R_2$), 800 bp ($F_1$–$R_3$), 1.3 Kb, ($F_1$–$R_4$), 1.8 Kb ($F_1$–$R_5$), and 2.3 Kb ($F_1$–$R_6$) are expected to be substantially absent in samples from the untreated tissue specimen taken from the normal animal. More particularly, a very light band, or no band at all, is expected for the 200 bp fragment ($F_1$–$R_1$), and no other bands, especially those corresponding to longer fragments, are expected. A similar pattern is expected for samples from the tissue specimen treated with the drug candidate from the normal animal.

In this case, the pattern of bands, representing the fragments amplified with the various primer pairs, is used as the marker of high integrity nucleic acid, and, thus, drug candidate activity. If the drug candidate has activity, the profile of amplified high integrity nucleic acid obtained from samples taken from treated tissue specimens of the diseased animal will be different from that of samples from the untreated tissue specimen from the diseased animal. More particularly, if the drug candidate has an activity, fewer bands and/or lighter bands will be seen in samples taken from treated tissue specimens from diseased animals relative to samples from the untreated tissue specimen from the diseased animal. The stronger the activity of the drug candidate, the fewer the bands that will be seen and/or the lighter the bands that will be seen. It is expected that the most powerfully active drug candidates will produce a band pattern similar to that of samples from the tissue specimen taken from the normal animal. Moreover, during the time course of the experiment, samples taken from the treated tissue specimen of the diseased animal over the time course will show changes in the number and/or level of intensity of the bands that are seen, if the drug candidate is active. These expected results are shown in Table 8, below.

TABLE 8

Hypothetical expected results at the amplified target.

| | Sample Taken at 2 Hours | Sample Taken at 4 Hours | Sample Taken at 6 Hours | Sample Taken at 8 hours |
|---|---|---|---|---|
| Tissue Specimen 1 from Diseased Animal 1 | Bands greater than 800 bp contain less nucleic acid than in initial sample | Bands greater than 800 bp missing | Bands between 200 bp and 800 bp contain less nucleic acid than in initial sample | Mainly a band at 200 bp |
| Tissue Specimen 2 from Diseased Animal 2 | No difference from initial sample (presence of high integrity nucleic) | Bands greater than 800 bp contain less nucleic acid than in initial sample | Bands greater than 800 bp contain less nucleic acid than in initial sample | Bands between 200 bp and 800 bp contain less nucleic acid than in initial sample |
| Tissue Specimen 3 from Diseased Animal 3 | Bands greater than 800 bp contain less nucleic acid than in initial sample | Bands greater than 800 bp missing | Bands between 200 bp and 800 bp contain less nucleic acid than in initial sample | Mainly a band at 200 bp |
| Untreated Tissue Specimen from Diseased Animal | No difference from initial sample (presence of high integrity nucleic acid) | No difference from initial sample (presence of high integrity nucleic acid) | No difference from initial sample (presence of high integrity nucleic acid) | No difference from initial sample (presence of high integrity nucleic acid) |
| Untreated Tissue Specimen from Normal Animal | No difference from initial sample (no high integrity nucleic acid) | No difference from initial sample (no high integrity nucleic acid) | No difference from initial sample (no high integrity nucleic acid) | No difference from initial sample (no high integrity nucleic acid) |
| Treated Tissue Specimen from Normal Animal | No difference from initial sample (no high integrity nucleic acid) | No difference from initial sample (no high integrity nucleic acid) | No difference from initial sample (no high integrity nucleic acid) | No difference from initial sample (no high integrity nucleic acid) |

Drug candidates that are promising can be studied further. For example, the same experiment can be run by treating tissue specimens from diseased animals with various doses of a particular drug candidate, and comparing the pattern of amplified fragments in samples taken from these treated tissue specimens with the pattern obtained from samples taken from tissue specimens from untreated diseased animals and with normal animals, as described above. A dose-response curve can be constructed to represent the effects of drug candidate dosage on drug candidate activity.

What is claimed is:

1. A method for screening drug activity, the method comprising the steps of:
    (a) determining a baseline level of high integrity nucleic acid associated with a nucleic acid locus in a first sample obtained from a patient having a disease or at least one indicium of a disease, wherein the high integrity nucleic acid is derived from a genome of the patient and the disease comprises at least one of cancer, pre-cancer, a disease associated with apoptosis, and a disease associated with programmed cell death;
    (b) treating the patient with a drug candidate; and
    (c) determining whether the high integrity nucleic acid associated with the nucleic acid locus in a second sample obtained from the patient is reduced.

2. The method of claim 1 wherein the determining steps comprise amplifying a target nucleic acid to determine the presence of high integrity nucleic acid in the samples.

3. The method of claim 2 wherein the target nucleic acid is amplified with one forward primer and at least two reverse primers.

4. The method of claim 2 wherein the target nucleic acid is amplified with at least two pairs of forward and reverse primers.

5. The method of claim 1 wherein the determining steps comprise capturing the high integrity nucleic acid.

6. The method of claim 5 wherein the high integrity nucleic acid is captured on a support-based complementary nucleic acid probe.

7. The method of claim 1 wherein a positive screen is determined by the presence of a lower amount of high integrity nucleic acid in the second sample relative to an amount of high integrity nucleic acid in the first sample.

8. The method of claim 1 wherein the samples are selected from the group consisting of stool, sputum, pus, blood serum, blood plasma, urine, saliva, colostrum, bile, and pancreatic juice.

9. The method of claim 7 wherein a positive screen indicates activity of the drug candidate.

10. The method of claim 7 wherein a positive screen indicates induction of programmed cell death.

11. The method of claim 7 wherein a positive screen indicates induction of apoptotic activity.

12. The method of claim 1 wherein the drug candidate comprises a nucleic acid.

13. The method of claim 1 wherein the drug candidate comprises a peptide.

14. The method of claim 1 wherein the drug candidate comprises a chemical compound.

15. The method of claim 1 wherein the drug candidate comprises a candidate for an anti-cancer drug.

16. The method of claim 1 wherein activity of a drug candidate is predictive of alleviation of disease symptoms by the drug candidate.

17. The method of claim 1 wherein at least one of the samples is contained in a buffer comprising at least 150 mM EDTA.

18. A method for screening drug activity, the method comprising the steps of:
   (a) determining a baseline level of high integrity nucleic acid associated with a nucleic acid locus in a sample from a subject having a disease or at least one indicium of a disease, wherein the high integrity nucleic acid is derived from a genome of the subject and the disease comprises at least one of cancer, pre-cancer, a disease associated with apoptosis, and a disease associated with programmed cell death;
   (b) treating the sample with a drug candidate; and
   (c) determining whether high integrity nucleic acid associated with the nucleic acid locus in the sample is reduced.

19. The method of claim 18 wherein the step of treating is performed ex vivo.

20. The method of claim 18 wherein the subject comprises an animal model of a disease.

21. The method of claim 18 wherein the sample is contained in a buffer comprising at least 150 mM EDTA.

22. A method for screening drug activity, the method comprising the steps of:
   (a) determining a baseline level of high integrity nucleic acid associated with a n nucleic acid locus in a sample from an animal model of a disease or an animal model that displays at least one indicium of a disease, wherein the high integrity nucleic acid is derived from a genome of the animal model and the disease comprises at least one of cancer, pre-cancer, a disease associated with apoptosis, and a disease associated with programmed cell death;
   (b) treating the animal model with a drug candidate; and
   (c) determining whether the high integrity nucleic acid associated with the nucleic acid locus in a second sample obtained from the animal model is reduced.

23. The method of claim 22 wherein the sample is contained in a buffer comprising at least 150 mM EDTA.

24. The method of claim 1 wherein the nucleic acid locus is selected from the group consisting of a coding region of a gene, a portion of a coding region of a gene, a noncoding region of a gene, a portion of a noncoding region of a gene, a regulatory element of a gene, a portion of a regulatory element of a gene, an RNA, and a fragment of genomic DNA.

25. The method of claim 1 wherein the patient is a human.

26. The method of claim 18 wherein the subject is an animal model of a disease.

* * * * *

SEQUENCE LISTING

<160> NUMBER OF SEQ ID NOS:   11

<210> SEQ ID NO 1
<211> LENGTH: 37
<212> TYPE: DNA
<213> ORGANISM: Artificial
<220> FEATURE:
<223> OTHER INFORMATION: K-ras probe

<400> SEQUENCE: 1
gtggagtatt tgatagtgta ttaaccttat gtgtgac                             37

<210> SEQ ID NO 2
<211> LENGTH: 37
<212> TYPE: DNA
<213> ORGANISM: Artificial
<220> FEATURE:
<223> OTHER INFORMATION: APC-1309

<400> SEQUENCE: 2
ttccagcagt gtcacagcac cctagaacca aatccag                             37

<210> SEQ ID NO 3
<211> LENGTH: 37
<212> TYPE: DNA
<213> ORGANISM: Artificial
<220> FEATURE:
<223> OTHER INFORMATION: APC-1378

<400> SEQUENCE: 3
cagatagccc tggacaaaca atgccacgaa gcagaag                             37

<210> SEQ ID NO 4
<211> LENGTH: 37
<212> TYPE: DNA
<213> ORGANISM: Artificial
<220> FEATURE:
<223> OTHER INFORMATION: p53 probe

<400> SEQUENCE: 4
tactcccctg ccctcaacaa gatgttttgc caactgg                             37

<210> SEQ ID NO 5
<211> LENGTH: 35
<212> TYPE: DNA
<213> ORGANISM: Artificial
<220> FEATURE:
<223> OTHER INFORMATION: p53 probe

<400> SEQUENCE: 5
atttcttcca tactactacc catcgacctc tcatc                               35

<210> SEQ ID NO 6
<211> LENGTH: 37
<212> TYPE: DNA
<213> ORGANISM: Artificial
<220> FEATURE:
<223> OTHER INFORMATION: p53 probe

```
-continued

<400> SEQUENCE: 6
atgaggccag tgcgccttgg ggagacctgt ggcaagc                              37

<210> SEQ ID NO 7
<211> LENGTH: 37
<212> TYPE: DNA
<213> ORGANISM: Artificial
<220> FEATURE:
<223> OTHER INFORMATION: p53 probe

<400> SEQUENCE: 7
gaaaggacaa gggtggttgg gagtagatgg agcctgg                              37

<210> SEQ ID NO 8
<211> LENGTH: 37
<212> TYPE: DNA
<213> ORGANISM: Artificial
<220> FEATURE:
<223> OTHER INFORMATION: BRCA1 probe

<400> SEQUENCE: 8
gattctgaag aaccaactt gtccttaact agctctt                               37

<210> SEQ ID NO 9
<211> LENGTH: 37
<212> TYPE: DNA
<213> ORGANISM: Artificial
<220> FEATURE:
<223> OTHER INFORMATION: BRCA2 probe

<400> SEQUENCE: 9
ctaagtttga atccatgctt tgctcttctt gattatt                              37

<210> SEQ ID NO 10
<211> LENGTH: 37
<212> TYPE: DNA
<213> ORGANISM: Artificial
<220> FEATURE:
<223> OTHER INFORMATION: APC1

<400> SEQUENCE: 10
cagatagccc tggacaaacc atgccaccaa gcagaag                              37

<210> SEQ ID NO 11
<211> LENGTH: 37
<212> TYPE: DNA
<213> ORGANISM: Artificial
<220> FEATURE:
<223> OTHER INFORMATION: APC2

<400> SEQUENCE: 11
gaagttcctg gattttctgt tgctggatgg tagttgc                              37
```